(12) United States Patent
Yun et al.

(10) Patent No.: US 11,383,084 B2
(45) Date of Patent: Jul. 12, 2022

(54) TREATMENT OF DERMATOLOGICAL CONDITIONS VIA NEUROMODULATION

(71) Applicant: Palo Alto Investors, Palo Alto, CA (US)

(72) Inventors: Anthony Joonkyoo Yun, Menlo Park, CA (US); Kimberly A. Bazar, Palo Alto, CA (US); Conrad Minkyoo Yun, San Mateo, CA (US)

(73) Assignee: Palo Alto Investors, Palo Alto, CA (US)

( * ) Notice: Subject to any disclaimer, the term of this patent is extended or adjusted under 35 U.S.C. 154(b) by 407 days.

(21) Appl. No.: 15/965,209

(22) Filed: Apr. 27, 2018

(65) Prior Publication Data

US 2018/0311499 A1 Nov. 1, 2018

Related U.S. Application Data

(60) Provisional application No. 62/491,152, filed on Apr. 27, 2017.

(51) Int. Cl.
*A61N 1/36* (2006.01)
*A61K 45/06* (2006.01)
*A61P 17/02* (2006.01)
*A61P 17/06* (2006.01)
*A61P 17/10* (2006.01)
*A61N 1/372* (2006.01)
*A61K 31/00* (2006.01)

(52) U.S. Cl.
CPC .......... *A61N 1/36017* (2013.01); *A61K 31/00* (2013.01); *A61K 45/06* (2013.01); *A61N 1/37264* (2013.01); *A61P 17/02* (2018.01); *A61P 17/06* (2018.01); *A61P 17/10* (2018.01)

(58) Field of Classification Search
CPC . A61N 1/36017; A61N 1/37264; A61P 17/10; A61P 17/06; A61P 17/02; A61K 31/00; A61K 45/06
See application file for complete search history.

(56) References Cited

U.S. PATENT DOCUMENTS

| 2004/0202706 A1* | 10/2004 | Koo | A61K 8/0208 |
| | | | 424/449 |
| 2006/0206149 A1* | 9/2006 | Yun | A61N 1/326 |
| | | | 607/3 |
| 2007/0287733 A1* | 12/2007 | Snorrason | A61K 31/445 |
| | | | 514/319 |

(Continued)

OTHER PUBLICATIONS

Inami et al., Surfactant-induced chronic pruritus: Role of L-histidine decarboxylase expression and histamine production in epidermis, Acta Derm Venereol. Nov. 2014;94(6):645-50; Abstract Only.

(Continued)

*Primary Examiner* — Catherine M Voorhees
*Assistant Examiner* — Roland Dinga
(74) *Attorney, Agent, or Firm* — Peter W. Schroen; Bret E. Field; Bozicevic, Field & Francis LLP

(57) ABSTRACT

Methods for treating a subject for a dermatological condition are provided. Aspects of the invention include administering an effective amount of a neuromodulatory agent to a subject to treat the subject for the dermatological condition. Also provided are compositions, kits and systems for practicing the subject methods.

6 Claims, 1 Drawing Sheet

(56) References Cited

U.S. PATENT DOCUMENTS

| | | | | |
|---|---|---|---|---|
| 2008/0317679 | A1* | 12/2008 | Tamarkin | A61K 9/12 424/45 |
| 2010/0222734 | A1* | 9/2010 | Jayes | A61N 1/0492 604/20 |
| 2010/0260669 | A1* | 10/2010 | Yun | A61P 11/06 424/1.49 |
| 2011/0144032 | A1* | 6/2011 | Hovens | A61P 13/08 514/19.5 |
| 2012/0142605 | A1* | 6/2012 | Hooper | A61K 31/57 514/18.6 |
| 2013/0064777 | A1* | 3/2013 | Tamarkin | A61K 8/31 424/43 |
| 2013/0304141 | A1* | 11/2013 | Goodman | A61N 1/328 607/2 |
| 2015/0297574 | A1* | 10/2015 | Snorrason | A61K 31/00 514/319 |
| 2016/0317621 | A1* | 11/2016 | Bright | A61K 31/19 |
| 2018/0117148 | A1* | 5/2018 | Holman | A61K 39/3955 |

OTHER PUBLICATIONS

Malekzad et al., Efficacy of oral naltrexone on pruritus in atopic eczema: a double-blind, placebo-controlled study, J Eur Acad Dermatol Venereol. Aug. 2009;23(8):948-50; Abstract Only.

Heyer et al., Efficacy of naltrexone on acetylcholine-induced alloknesis in atopic eczema, Exp Dermatol. Oct. 2002; 11 (5):448-55; Abstract Only.

Yamashita et al., Treatment of the chronic itch of atopic dermatitis using standard drugs and kampo medicines, Biol Pharm Bull. 2013;36(8):1253-7.

Liu et al., Effect of matrine on the expression of substance P receptor and inflammatory cytokines production in human skin keratinocytes and fibroblasts, Int Immunopharmacol. Jun. 2007;7(6):816-23; Abstract Only.

Wollina et al., Botulinum toxin in dermatology—beyond wrinkles and sweat, J Cosmet Dermatol. Dec. 2005;4 (4):223-7; Abstract Only.

Hamada et al., Neuronal conditions of spinal cord in dermatitis are improved by olopatadine, Eur J Pharmacol. Oct. 10, 2006;547(1-3):45-51; Abstract Only.

Stander et al., Antipruritic effects of pimecrolimus and tacrolimus, Hautarzt. May 2003;54(5):413-7; Abstract Only.

Wollina et al., Adjuvant botulinum toxin A in dyshidrotic hand eczema: a controlled prospective pilot study with left-right comparison, J Eur Acad Dermatol Venereol. Jan. 2002;16(1):40-2; Abstract Only.

Bozkurt et al., Inhibitory effect of the methanolic extract of Verbascum latisepalum Hub.-Mor. on endothelium-dependent relaxation in rat thoracic aorta, Zeitschrift fur Naturforschung. C, Journal of Biosciences, May 1, 2014, 69 (5-6):219-225.

Takizawa et al., VUF-K-8788, a periphery-selective histamine H1 antagonist with anti-pruritic activities, Jpn J Pharmacol. May 2001;86(1):55-64.

Groene et al., Doxepin affects acetylcholine induced cutaneous reactions in atopic eczema, Exp Dermatol. Apr. 2001;10(2):110-7; Abstract Only.

El-Nour et al., The expression and functional significance of the serotonin(2C) receptor in murine contact allergy, Exp Dermatol. Aug. 2007;16(8):644-50; Abstract Only.

Zenker et al., Therapy of pruritus associated with skin diseases with the serotonin receptor antagonist ondansetron, J Dtsch Dermatol Ges. Sep. 2003;1(9):705-10; Abstract Only.

* cited by examiner

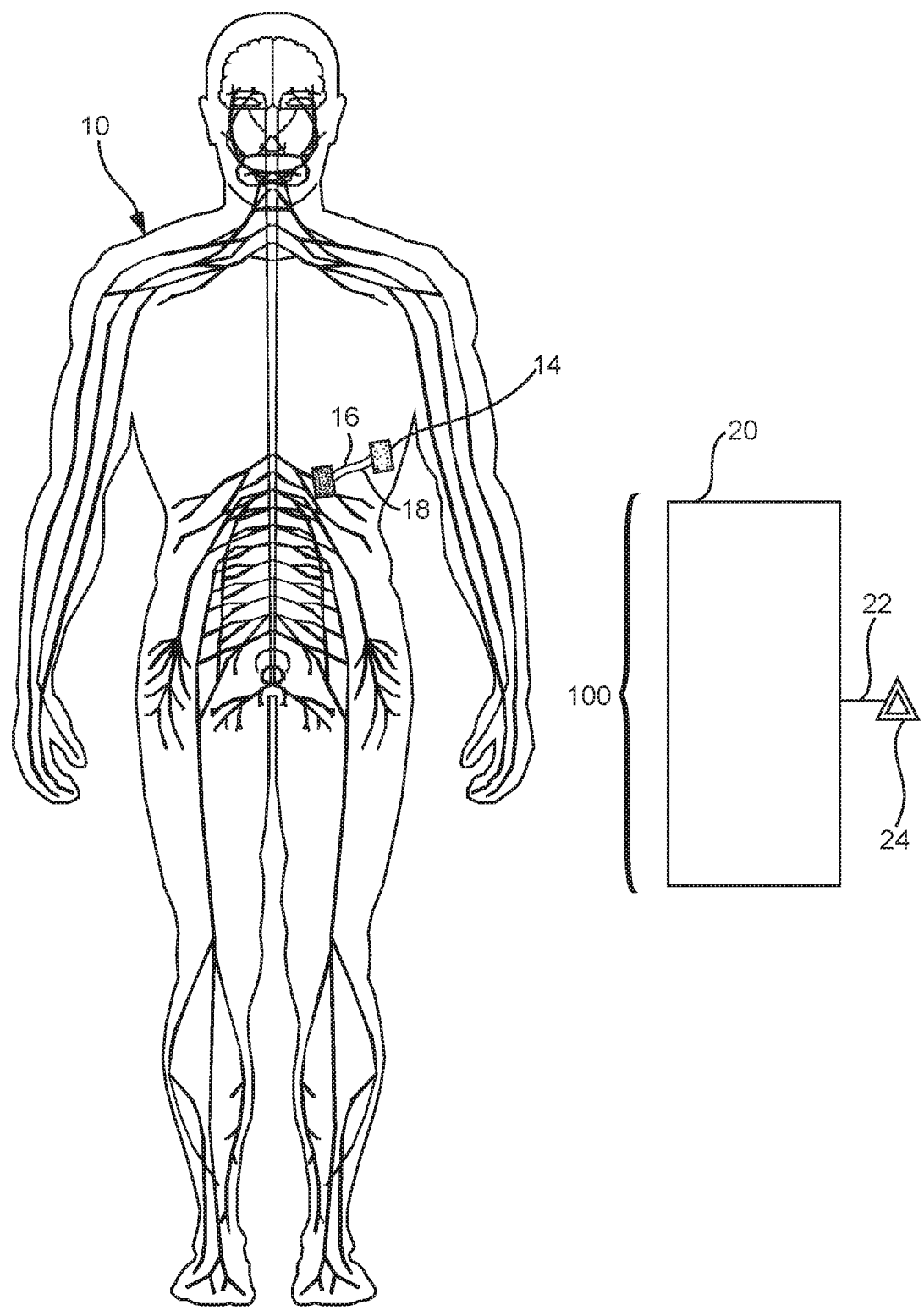

TREATMENT OF DERMATOLOGICAL CONDITIONS VIA NEUROMODULATION

CROSS-REFERENCE TO RELATED APPLICATIONS

Pursuant to 35 U.S.C. § 119 (e), this application is claims priority to U.S. Patent Provisional Patent Application Ser. No. 62/491,152 filed Apr. 27, 2017; the disclosure of which is herein incorporated by reference.

INTRODUCTION

The skin is a complex multi-layered organ. The outer layer of the skin is the epidermis having a thickness of between 0.05 mm (eyelids) and 1.5 mm (palms and soles) made up of keratinocytes, melanocytes, Langerhans cells, and Merkel cells in five layers. Under the epidermis is the dermis having a thickness of 0.3 mm (eyelids) to 3 mm (back), primarily comprising collagen, elastic fibers and extrafibrillar matrix in two layers, the upper papillary layer and the lower reticular layer. Under the dermis is the hypodermis housing large blood vessels and nerves primarily comprising fibroblasts, adipose cells, and macrophages.

Dermatological conditions are diseases, disorders, symptoms, etc. involving the skin. A non-limiting list of dermatological conditions include, but are not limited to: dermatitis, e.g., atopic dermatitis, allergic contact dermatitis, irritant contact dermatitis, radiation dermatitis, seborrheic dermatitis; psoriasis; sunburn; ulcers, e.g., diabetic ulcers, pressure ulcers, and stasis ulcers; acne; rosacea; Rhytides (wrinkles); Hyperhidrosis (excessive sweating); hyperpigmentation; etc. Dermatological conditions can also arise from irritation and/or pain following laser or chemical resurfacing, dermabrasion therapy, cuts, burns, and abrasions. Each dermatological condition, irrespective of cause, is associated with various symptoms, such as erythema, pruritus, exudation, excoriation, and lichenification.

SUMMARY

Methods for treating a subject for a dermatological condition are provided. Aspects of the invention include administering an effective amount of a neuromodulatory agent to a subject to treat the subject for the dermatological condition. Also provided are compositions, kits and systems for practicing the subject methods.

BRIEF DESCRIPTIONS OF THE DRAWINGS

FIG. 1 shows an exemplary embodiment of an electric energy applying device operatively positioned in a subject's body in accordance with embodiments of the subject methods.

DESCRIPTION OF THE REPRESENTATIVE EMBODIMENTS

Methods for treating a subject for a dermatological condition are provided. Aspects of the invention include administering an effective amount of a neuromodulatory agent to a subject to treat the subject for the dermatological condition. Also provided are compositions, kits and systems for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Aspects of the invention include methods of treating a subject for a dermatological condition. Dermatological conditions are diseases, disorders, symptoms, etc. involving the skin. By treatment is meant that at least an amelioration of the symptoms associated with the dermatological condition afflicting the subject (i.e., host) is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

As summarized above, in practicing the subject methods, an effective amount of a neuromodulatory agent is administered to the subject to treat the subject for the dermatological condition. Accordingly, embodiments of the subject methods include administering an effective amount, i.e., a therapeutically effective amount, of one or more pharmacological agents or electrical stimuli to a subject. By "effective amount" is meant a dosage sufficient to cause the subject to mount a compensatory response effective to treat the subject, as desired. The effective amount will vary with the age and physical condition of the subject, severity of the condition being treated, the duration of the treatment, the nature of any concurrent treatment, the pharmaceutically acceptable carrier used if any, and analogous factors within the knowledge and expertise of those skilled in the art.

The term "neuromodulatory agent" is used broadly to refer to any agent, which agent may be a pharmacological or electrical agent (i.e., electrical stimulus), to influence or change nervous system activity, e.g., in a manner effective to treat a target dermatological condition. Accordingly, neuromodulatory agents that may be employed in method of the invention include pharmacological agents having neuromodulatory activity. Pharmacological agents having neuromodulatory activity that may be employed in methods of the invention include, but are not limited to: cholinergic system modulators, serotonin system modulators, dopamine system modulators, noradrenaline system modulators, histamine system modulators, neuropeptide system modulators, substance P system modulators, adenosine system modulators, GABA system modulators, opioid peptides system modulators, oxytocin system modulators, etc.

Cholinergic system modulators that may be employed in embodiments of the invention include, but are not limited to: acetylcholine, atropine, ambenonium, arecholine, atropine methyl-nitrate, benztropine, bethanechol, biperiden, botulinum toxin, carbachol, cevimeline, curare (d-Tubocurarine), cyclopentolate, demecarium, echothiophate, edrophonium, glycopyrrolate, hemicholinium, hexamethonium, homatropine, ipratropium, isoflurophate (DFP), malathion, mecamylamine, methacholine, methscopolamine, muscarine, neostigmine, nicotine, parathion, physostigmine, pilocarpine, pirenzepine, propantheline, pyridostigmine, sarin, scopolamine, soman, succinylcholine, tabun, trihexyphenidyl, trimethaphan, tropicamide, varenicline, galantamine hydrobromide, suxamethonium chloride, epibatidine, atracurium, doxacurium, mivacurium, pancuronium, tubocurarine, vecuronium, 18-methoxycoronaridine, dextromethorphan, dextrorphan, 3-methoxymorphinan, oxotremorine, dicyclomine, doxylamine, orphenadrine, oxitropium, oxybutynin, tolterodine, tiotropium, solifenacin, bupropion, hyoscyamine, ambenomium, donezepil, rivastigmine, tacrine, pralidoxime, cisatracurium, metocurine, rocuronium, oxybutynine, trospium, dihexyverine, prifinium, propantheline, tiemonium, benzhexol, tropatepine, biperidene, and botulinum toxin.

Serotonin system modulators that may be employed in embodiments of the invention include, but are not limited to: alaproclate, cericlamine, citalopram, dapoxetine, escitalopram, femoxetine, fluoxetine, fluvoxamine, ifoxetine, indalpine, omiloxetine, panuramine, paroxetine, pirandamine, RTI-353, sertraline, zimelidine, desmethylcitalopram, didesmethylcitalopram, seproxetine, cianopramine, litoxetine, lubazodone, SB-649,915, nefazodone, trazodone, vilazodone, vortioxetine, dextromethorphan, dextropropoxyphene, dimenhydrinate, diphenhydramine, mepyramine, mifepristone, delucemine, mesembrenone, mesembrine, roxindole, amitriptyline, amitriptylinoxide, amoxapine, butriptyline, clomipramine, dimetacrine, desipramine, dibenzepin, demexiptiline, dosulepin, doxepin, imipramine, imipraminoxide, iprindole, lofepramine, melitracen, metapramaine, nitroxazepine, nortriptyline, noxiptiline, pipofezine, propizepine, protriptyline, quinupramine, trimipramine, isocarboxazid, nialamide, phenelzine, hydracarbazine, tranylcypromine, bifemelane, moclobemide, pirlindole, toloxatone, rasagiline, selegiline, linezolid, methylene blue, etoperidone, lorpiprazole, lubazodone, mepiprazole, nefazodone, trazodone, medifoxamine, buspirone, trazodone, cisapride, ergotamine, agomelatine, ipsapirone, gepirone, methysergide, risperidone, spiperone, ritanerin, BMY 7378, NAN 190, SDZ 216525, DHE, 5-benzyloxytryptamine, y-methyl, LY-53857, MK 212, MCPP, ondomestron, tandospirone, LSD, mescaline, 2C-B, fenfluramine, pergolide, cabergoline, AS-19, cisapride, tegaserod, prucalopride, lorcaserin, MDMA, LY-334,370, 8-OH DPAT, renzapride, donitriptan hydrochloride, eletriptan hydrobromide, GR 46611, L-694,247, L-703,664 succinate, PNU 109291, PNU 142633, sumatriptan, rizatriptan, zolmitriptan, a triptan, alosetron, ondansetron, palonosetron, granisetron, dolasetron, zacopride, CP 135807, 8-OH-DPAT, flesinoxan, RU 24,969, bufotenine, tryptamine, mesulergine, quipazine, BW-501, 1-(2,5-dimethoxy-4-methylphenyl)-2-aminopropane, ICS-205,930, pizotifen, oxetorone, lysergide, psilocybine, selective serotonin reuptake inhibitors (SSRIs), tricyclic antidepressants, and monoamine oxidase inhibitors.

Dopamine system modulators that may be employed in embodiments of the invention include, but are not limited to: brexipiprazole, AMPT, carbidopa, amantadine, memantine, rimantadine, 7-OH-DPAT, 8-OH-PBZI, rotigotine, UH-232, 6-Br-APB, fenoldopam, SKF-38,393, SKF-77,434, SKF-81,297, SKF-82,958, SKF-83,959, bromocriptine, cabergoline, dihydroergocryptine, lisuride, pergolide, 2-OH-NPA, A-86,929, ciladopa, dihydrexidine, dinapsoline, dinoxyline, doxanthrine, A-68,930, A-77,636, A-412,997, ABT-670, ABT-724, aplindore, apomorphine, aripiprazole, bifeprunox, BP-897, CY-208,243, dizocilpine, etilevodopa, flibanserin, ketamine, melevodopa, modafinil, pardoprunox, phencyclidine, PD-128,907, PD-168,077, PF-219,061, piribedil, pramipexole, propylnorapomorphine, pukateine, quinagolide, quinelorane, quinpirole, RDS-127, Ro10-5824, ropinirole, rotigotine, roxindole, salvinorin A, SKF-89,145, sumanirole, terguride, umespirone, WAY-100,635, acepromazine, azaperone, benperidol, bromperidol, clopenthixol, chlorpromazine, chlorprothixene, droperidol, flupentixol, fluphenazine, fluspirilene, haloperidol, loxapine, mesoridazine, methotrimeprazine, nemonapride, penfluridol, perazine, periciazine, perphenazine, pimozide, prochlorperazine, promazine, sulforidazine, sulpiride, sultopride, thioridazine, thiothixene, trifluoperazine, triflupromazine, trifluperidol, zuclopenthixol, amisulpride, asenapine, blonanserin, cariprazine, carpipramine, clocapramine, clozapine, gevotroline, iloperidone, lurasidone, melperone, molindone, mosapramine, ocaperidone, olanzapine, paliperidone, perospirone, piquindone, quetiapine, remoxipride, risperidone, sertindole, tiospirone, ziprasidone, zotepine, AS-8112, alizapride, bromopride, clebopride, domperidone, metoclopramide, thiethylperazine, amoxapine, buspirone, butaclamol, ecopipam, N-Ethoxycarbonyl-2-ethoxy-1,2-dihydroquinoline (EEDQ), eticlopride, fananserin, L-745,870, nafadotride, nuciferine, PNU-99,194, raclopride, sarizotan, SB-277,011-A, SCH-23,390, SKF-83,566, SKF-83,959, sonepiprazole, spiperone, spiroxatrine, stepholidine, tetrahydropalmatine, tiapride, UH-232, yohimbine, DBL-583, GBR-12,935, nefazodone, vanoxerine, 1-(1-(1-benzothiophen-2-yl)cyclohexyl)piperidine (BTCP), desoxypipradrol, dextromethylphenidate, difemetorex, ethylphenidate, methylnaphthidate, methylphenidate, phencyclidine, pipradrol, diphenylprolinol, methylenedioxypyrovalerone (MDPV), naphyrone, prolintane, pyrovalerone, 3β-(4'-chlorophenyl)-2β-(3'-phenylisoxazol-5'-yl)tropane (β-CPPIT), altropane, brasofensine, WIN 35428 (β-CFT), dichloropane, difluoropine, N-(2'-fluoroethyl-)-3β-(4'-chlorophenyl)-2β-(3'-phenylisoxazol-5'-yl)nortropane (FE-β-CPPIT), N-(3'-fluoropropyl-)-3β-(4'-chlorophenyl)-2β-(3'-phenylisoxazol-5'-yl)nortropane (FP-β-CPPIT), Ioflupane ($^{123}$I), Iometopane, RTI-112, RTI-113, RTI-121, RTI-126, RTI-150, RTI-177, RTI-229, RTI-336, tenocyclidine, tesofensine, troparil, tropoxane, 2β-propanoyl-3β-(4-tolyl)-tropane (WF-11), 2β-propanoyl-3β-(2-naphthyl)-tropane (WF-23), 2-propanoyl-3-(4-isopropylphenyl)-tropane (WF-31), 2α-(propanoyl)-3β-(2-(6-methoxynaphthyl))-tropane (WF-33), adrafinil, armodafinil, amfonelic acid, amineptine, benzatropine (benztropine), bromantane, 2-butyl-3-(p-tolyl)quinuclidine (BTQ), BTS-74,398, bupropion (amfebutamone), ciclazindol, diclofensine, dimethocaine, diphenylpyraline, dizocilpine, DOV-102,677, DOV-21,947, DOV-216,303, etybenzatropine (ethylbenztropine), EXP-561, fencamine, fencamfamine, fezolamine, GYKI-52,895, hydrafinil, indatraline, ketamine, lefetamine, levophacetoperane, LR-5182, manifaxine, mazindol, medifoxamine, mesocarb, modafinil, nefopam, nomifensine, NS-2359, O-2172, pridefrine, propylamphetamine, radafaxine, SEP-225,289, SEP-227,162, sertraline, sibutramine, tametraline, tripelennamine, fenbutrazate, morazone, phendimetrazine, phenmetrazine, 4-methylaminorex (4-MAR, 4-MAX), aminorex, clominorex, cyclazodone, fenozolone, fluminorex, pemoline, thozalinone, 2-hydroxyphenethylamine (2-OH-PEA), 4-chlorophenylisobutylamine (4-CAB), 4-methylamphetamine (4-MA), 4-methylmethamphetamine (4-MMA), alfetamine, amfecloral, amfepentorex, amfepramone, amphetamine (dextroamphetamine, levoamphetamine), amphetaminil, β-methylphenethylamine (β-Me-PEA), benzodioxolylbutanamine (BDB), benzodioxolylhydroxybutanamine (BOH), benzphetamine, buphedrone, butylone, cathine, cathinone, clobenzorex, clortermine, D-deprenyl, dimethoxyamphetamine (DMA), dimethoxymethamphetamine (DMMA), dimethylamphetamine, dimethylcathinone (dimethylpropion, metamfepramone), ethcathinone (ethylpropion), ethylamphetamine, ethylbenzodioxolylbutanamine (EBDB), ethylone, famprofazone, fenethylline, fenproporex, flephedrone, fludorex, furfenorex, hordenine, lophophine (homomyristicylamine), mefenorex, mephedrone, methamphetamine (desoxyephedrine, methedrine; dextromethamphetamine, levomethamphetamine), methcathinone (methylpropion), methedrone, methoxymethylenedioxyamphetamine (MMDA), methoxymethylenedioxymethamphetamine (MMDMA), methylbenzodioxolylbutanamine (MBDB), methylenedioxyamphetamine (MDA, tenamfetamine), methylenedioxyethylamphetamine (MDEA), methylenedioxyhydroxyamphetamine (MDOH), methylenedioxymethamphetamine (MDMA), methylenedioxymethylphenethylamine (MDMPEA, homarylamine), methylenedioxyphenethylamine (MDPEA, homopiperonylamine), methylone, ortetamine, parabromoamphetamine (PBA), parachloroamphetamine (PCA), parafluoroamphetamine (PFA), parafluoromethamphetamine (PFMA), parahydroxyamphetamine (PHA), paraiodoamphetamine (PIA), paredrine (norpholedrine, oxamphetamine), phenethylamine (PEA), pholedrine, phenpromethamine, prenylamine, propylamphetamine, tiflorex (flutiorex), tyramine (TRA), xylopropamine, zylofuramine, 2,5-dimethoxy-4-bromobenzylpiperazine (2C-B-BZP), benzylpiperazine (BZP), methoxyphenylpiperazine (MeOPP, paraperazine), methylbenzylpiperazine (MBZP), methylenedioxybenzylpiperazine (MDBZP, piperonylpiperazine), 2-amino-1,2-dihydronaphthalene (2-ADN), 2-aminoindane (2-AI), 2-aminotetralin (2-AT), 4-benzylpiperidine (4-BP), 5-Iodo-2-aminoindane (5-IAI), clofenciclan, cyclopentamine, cypenamine, cyprodenate, feprosidnine, gilutensin, heptaminol, hexacyclonate, indanylaminopropane (IAP), indanorex, isometheptene, methylhexanamine, naphthylaminopropane (NAP), octodrine, phthalimidopropiophenone, propylhexedrine (levopropylhexedrine), tuaminoheptane (tuamine), 3,4-dihydroxystyrene, 3-Iodotyrosine, aquayamycin, bulbocapnine, metirosine, oudenone, benserazide, genistein, methyldopa, deserpidine, ibogaine, reserpine, tetrabenazine, benmoxin, caroxazone, echinopsidine, furazolidone, hydralazine, indantadol, iproclozide, iproniazid, isocarboxazid, isoniazid, linezolid, mebanazine, metfendrazine, nialamide, octamoxin, paraxazone, phenelzine, pheniprazine, phenoxypropazine, pivalylbenzhydrazine, procarbazine, safrazine, tranylcypromine, amiflamine, bazinaprine, befloxatone, befol, brofaromine, cimoxatone, clorgiline, esuprone, harmala alkaloids (harmine, harmaline, tetrahydroharmine, harman, norharman, etc.), methylene blue, metralindole, minaprine, moclobemide, pirlindole, sercloremine, tetrindole, toloxatone, tyrima, d-deprenyl, selegiline (l-deprenyl), ladostigil, lazabemide, milacemide, mofegiline, pargyline, rasagiline, safinamide, entacapone, nitecapone, opicapone, tolcapone, bupicomide, disulfiram, dopastin, fusaric acid, nepicastat, phenopicolinic acid, tropolone, levodopa, benzofuranylpropylaminopentane (BPAP), phenylpropylaminopentane (PPAP), oxidopamine, and (6-hydroxydopamine).

Noradrenaline system modulators that may be employed in embodiments of the invention include, but are not limited to: acebutolol, albuterol, amineptine, amitriptyline, amphetamine, atenolol, betaxolol, bitoterol, bretylium, butoxamine, carteolol, clonidine, clorgyline, cocaine, deprenyl, dobutamine, dopamine, doxazosin, ephedrine, epinephrine, esmolol, guanabenz, guanadrel, guanethidine, guanfacine, imipramine, isoethanine, isoproterenol, labetalol, levobunolol, metaproterenol, metaraminol, methamphetamine, methoxamine, methyldopa, methylphenidate, metoprolol, nadolol, naphazoline, norepinephrine, oxymetolazine, pargyline, pemoline, penbutolol, phenmetrazine, phenoxybenzamine, phentolamine, phenylephrine, pindolol, pirbuterol, prazosin, propranolol, pseudoephedrine, reserpine, ritodrine, terazosin, terbutaline, timolol, tolazoline, tranylcypromine, tyramine, urapidil, xylometolazine, yohimbine, desipramine, dibenzepin, lofepramine, nortriptyline, protriptyline, amidephrine, anisodamine, anisodine, cirazoline, dipivefrine, dopamine, ephedrine, epinephrine (adrenaline), etilefrine, ethylnorepinephrine, 5-fluoronorepinephrine, 6-fluoronorepinephrine, indanidine, levonordefrin, midodrine, octopamine, oxymetazoline, phenylpropanolamine, pseudoephedrine, synephrine, tetrahydrozoline, abanoquil, adimolol, ajmalicine, alfuzosin, amosulalol, arotinolol, atiprosin, benoxathian, buflomedil, bunazosin, carvedilol, ci-926, corynanthine, dapiprazole, dl-017, domesticine, eugenodilol, fenspiride, gyki-12, 743, gyki-16, 084, indoramin, ketanserin, l-765, 314, labetalol, mephendioxan, metazosin, monatepil, moxisylyte (thymoxamine), naftopidil, nantenine, neldazosin, nicergoline, niguldipine, pelanserin, phendioxan, piperoxan, quinazosin, ritanserin, rs-97, 078, sgb-1, 534, silodosin, sl-89.0591, spiperone, talipexole, tamsulosin, tibalosin, tiodazosin, tipentosin, trimazosin, upidosin, zolertine, amitraz, apraclonidine, brimonidine, cannabivarin, detomidine, dexmedetomidine, dihydroergotamine, dipivefrine, dopamine, ergotamine, esproquin, etilefrine, ethylnorepinephrine, 6-fluoronorepinephrine, guanoxabenz, levonordefrin, lofexidine, medetomidine, methyldopa, mivazerol, naphazoline, 4-nemd, (r)-3-nitrobiphenyline, norepinephrine (noradrenaline), phenylpropanolamine, piperoxan, pseudoephedrine, rilmenidine, romifidine, talipexole, tetrahydrozoline, tizanidine, tolonidine, urapidil, xylazine, xylometazoline, adimolol, aptazapine, atipamezole, brl-44408, buflomedil, cirazoline, efaroxan, esmirtazapine, fenmetozole, fluparoxan, gyki-12, 743, gyki-16, 084, idazoxan, mianserin, mirtazapine, mk-912, nan-190, olanzapine, phentolamine, phenoxybenzamine, piperoxan, piribedil, pyrimidinylpiperazine, rauwolscine, rotigotine, sb-269, 970, setiptiline, spiroxatrine, sunepitron, tolazoline, abediterol, amibegron, arbutamine, arformoterol, arotinolol, bambuterol, befunolol, bitolterol, bromoacetylalprenololmenthane (baam), broxaterol, buphenine, carbuterol, cimaterol, clenbuterol, denopamine, deterenol, dipivefrine, dopexamine, ephedrine, epinephrine (adrenaline), etafedrine, etilefrine, ethylnorepinephrine, fenoterol, 2-fluoronorepinephrine, 5-fluoronorepinephrine, formoterol, hexoprenaline, higenamine, indacaterol, isoetarine, n-isopropyloctopamine, isoxsuprine, levonordefrin, levosalbutamol, mabuterol, methoxyphenamine, methyldopa, norepinephrine (noradrenaline), orciprenaline, oxyfedrine, phenylpropanolamine, prenalterol, ractopamine, procaterol, pseudoephedrine, quinterenol, reproterol, rimiterol, salmeterol, solabegron, tretoquinol, tulobuterol, xamoterol, zilpaterol, zinterol, adaprolol, adimolol, afurolol, alprenolol, alprenoxime, amosulalol, ancarolol, arnolol, arotinolol, befunolol, bevantolol, bisoprolol, bopindolol, bornaprolol, brefonalol, bucindolol, bucumolol, bufetolol, bufuralol, bunitrolol, bunolol, bupranolol, butaxamine, butidrine, butofilolol, capsinolol, carazolol, carpindolol, carvedilol, celiprolol, cetamolol, cicloprolol, cinamolol, cloranolol, cyanopindolol, dalbraminol, dexpropranolol, diacetolol, dichloroisoprenaline, dihydroalprenolol, dilevalol, diprafenone, draquinolol, ecastolol, epanolol, ericolol, ersentilide, esatenolol, eugenodilol, exaprolol, falintolol, flestolol, flusoxolol, hydroxycarteolol, hydroxytertatolol, ici-118, 551, idropranolol, indenolol, indopanolol, iodocyanopindolol, iprocrolol, isoxaprolol, isamoltane, labetalol, landiolol, levobetaxolol, levocicloprolol, levomoprolol, medroxalol, mepindolol, metalol, metipranolol, moprolol, nadoxolol, nafetolol, nebivolol, neraminol, nifenalol, nipradilol, oberadilol, oxprenolol, pacrinolol, pafenolol, pamatolol, pargolol, parodilol, penirolol, phqa-33, pindolol, pirepolol, practolol, primidolol, procinolol, pronethalol, propafenone, ridazolol, ronactolol, soquinolol, sotalol, spirendolol, sr 59230a, sulfinalol, ta-2005, talinolol, tazolol, teoprolol, tertatolol, tienoxolol, tilisolol, tiprenolol, tolamolol, toliprolol, tribendilol, trigevolol, xibenolol, xipranolol, amedalin, atomoxetine (tomoxetine), ciclazindol, daledalin, esreboxetine, lortalamine, mazindol, nisoxetine, reboxetine, talopram, talsupram, tandamine, viloxazine, bupropion (amfebutamone), fencamine, fencamfamine, lefetamine, levophacetoperane, lr-5182, manifaxine, nomifensine, o-2172, radafaxine, bicifadine, desvenlafaxine, duloxetine, eclanamine, levomilnacipran, milnacipran, sibutramine, venlafaxine, brasofensine, diclofensine, dov-102, 677, dov-21, 947, dov-216, 303, jnj-7925476, jz-iv-10, methylnaphthidate, naphyrone, ns-2359, prc200-ss, sep-225, 289, sep-227, 162, tesofensine, butriptyline, cianopramine, clomipramine, dosulepin, doxepin, melitracen, trimipramine, amoxapine, maprotiline, mianserin, oxaprotiline, setiptiline, cp-39, 332, exp-561, fezolamine, *Ginkgo biloba*, indeloxazine, nefazodone, nefopam, pridefrine, tapentadol, teniloxazine, tramadol, ziprasidone, ibogaine, tetrabenazine, bietaserpine, fenbutrazate, morazone, phendimetrazine, aminorex, clominorex, cyclazodone, fenozolone, fluminorex, 4-methylaminorex, thozalinone, 2-oh-pea, 4-cab, 4-fa, 4-fma, 4-ma, 4-mma, alfetamine, amfecloral, amfepentorex, amfepramone, dextroamphetamine, levoamphetamine, amphetaminil, β-me-pea, bdb, benzphetamine, boh, buphedrone, butylone, cathine, cathinone, clobenzorex, clortermine, dimethylamphetamine, dimethylcathinone (dimethylpropion, metamfepramone), dma, dmma, ebdb, ephedrine, ethcathinone, ethylamphetamine, ethylone, famprofazone, fenethylline, fenproporex, flephedrone, fludorex, furfenorex, hordenine, iap, imp, lisdexamfetamine, lophophine, mbdb, mda (tenamfetamine), mdea, mdma, mdmpea, mdoh, mdpea, mefenorex, mephedrone, mephentermine, dextromethamphetamine, levomethamphetamine, methcathinone, methedrone, methylone, nap, ortetamine, paredrine, pba, pca, pentorex (phenpentermine), phenethylamine, pholedrine, phenpromethamine, phentermine, phenylpropanolamine, pia, prenylamine, propylamphetamine, pseudoephedrine, selegiline (l-deprenyl), tiflorex, xylopropamine, zylofuramine, benzylpiperazine (bzp), 2, 5-dimethoxy-4-bromobenzylpiperazine (2c-b-bzp), methylbenzylpiperazine (mbzp), metachlorophenylpiperazine (mcpp), methylenedioxybenzylpiperazine (mdbzp), methoxyphenylpiperazine (meopp), parafluorophenylpiperazine (pfpp), 2-amino-1, 2-dihydronaphthalene, 2-aminoindane, 2-aminotetralin, 2-benzylpiperidine, 4-benzylpiperidine, clofenciclan, cyclopentamine, cypenamine, cyprodenate, feprosidnine, gilutensin, heptaminol, hexacyclonate, indanorex, 5-iodo-2-aminoindane (5-iai), isometheptene, methylhexanamine, octodrine, phthalimidopropiophenone, propylhexedrine, levopropylhexedrine, tuaminoheptane, 3, 4-dihydroxystyrene, 3-iodotyrosine, aquayamycin, bulbocapnine, metirosine, oudenone, benserazide, carbidopa, genistein, methyldopa, bupicomide, disulfiram, dopastin, fusaric acid, nepicastat, phenopicolinic acid, tropolone, cgs-19281a, skf-64139, skf-7698, benmoxin, caroxazone, echinopsidine, furazolidone, hydralazine, indantadol, iproclozide, iproniazid, isocarboxazid, isoniazid, linezolid, mebanazine, metfendrazine, nialamide, octamoxin, paraxazone, phenelzine, pheniprazine, phenoxypropazine, pivalylbenzhydrazine, procarbazine, safrazine, amiflamine, bazinaprine, befloxatone, befol, brofaromine, cimoxatone, clorgiline, esuprone, harmala alkaloids, harmine, harmaline, tetrahydroharmine, harman, norharman, methylene blue, metralindole, minaprine, moclobemide, pirlindole, sercloremine, tetrindole, toloxatone, tyrima, d-deprenyl, selegiline (l-deprenyl), ladostigil, lazabemide, milacemide, mofegiline, rasagiline, safinamide, entacapone, and tolcapone.

Histamine system modulators that may be employed in embodiments of the invention include, but are not limited to: acrivastine, azelastine, bilastine, bromodiphenhydramine, brompheniramine, buclizine, carbinoxamine, cetirizine, chlorodiphenhydramine, chlorphenamine, chlorpromazine, clemastine, cyclizine, cyproheptadine, dexbrompheniramine, chlorpheniramine, dexchlorpheniramine, dimenhydrinate, dimetindene, diphenhydramine, doxylamine ebastine, embramine, fexofenadine, hydroxyzine, loratadine, meclizine, mirtazapine, olopatadine, orphenadrine, phenindamine, pheniramine, phenyltoloxamine, promethazine, quetiapine, rupatadine, tripelennamine, triprolidine, levocetirizine, desloratadine, pyrilamine, cimetidine, famotidine, lafutidine, nizatidine, ranitidine, roxatidine, tiotidine, clobenpropit, ABT-239, ciproxifan, conessine, A-349,821, pitolisant, thioperamide, JNJ 7777120, VUF-6002, tritoqualine, catechin, cromolyn sodium, nedocromil, mepyramine, chloropyramine, antazoline, tripelennamine, doxylamine, bromazine, chlorcyclizine, alimemazine, azatadine, astemizole, ketotifen, mizolastine, bepotastine, quifenadine, levocabastine, 4-methylhistamine, VUF-8430, OUP-16, betazole, impromidine, betahistine, HTMT dimaleate, 2pyridylethylamine dihydrochloride, histamine dihydrochloride, amthamine dihydrobromide, dimaprit dihydrochloride, (R)-α-methylhistamine, cipralisant, imbutamine, immepip, imetit, immethridine, methimepip, proxyfan, proxyfan oxalate, burimamide, failproxifan impentamine, iodophenpropit, irdabisant, VUF-5681, JNJ 10191584 maleate, A 987306, A 943931 dihydrochloride, clobenpropit dihydrobromide, imetit dihydrobromide, immepip dihydrobromide, VUF 10460, VUF 8430 dihydrobromide, GSK189254, JNJ-5207852, and BF2.649.

Neuropeptide system modulators that may be employed in embodiments of the invention include, but are not limited to: endorphins, casomorphins, exorphins, rubiscolins, gluten exorphin, gluteomorphin, soymorphin-5, deltorphin I and II, dermorphin, enkephalins, dynorphins, enomorphins, adrenorphin, amidorphin, leumorphin, hemorphins, opiorphin, enkephalinase inhibitor, 3-HO-PCP, 7-PET, acetorphine, acetoxyketobemidone, acetyldihydrocodeine, acetylfentanyl, acetylmethadol, acetylmorphine, acetyl propionylmorphine, acrylfentanyl, AD-1211, adrenorphin, AH-7921, akuammine, alfentanil, alimadol, 3-allylfentanyl, allylnorpethidine, allylprodine, alphacetylmethadol, alphamethadol, alphamethylthiofentanyl, anileridine, azaprocin, azidomorphine, BDPC, benzethidine, benzhydrocodone, benzylmorphine, betacetylmethadol, betahydroxyfentanyl, betahydroxythiofentanyl, betamethadol, bezitramide, brifentanil, bromadoline, buprenorphine, buprenorphine/naloxone, butyrfentanyl, BW373U86, C-8813, 8-carboxamidocyclazocine, cyclazocine, carfentanil, cebranopadol, chloromorphide, chloroxymorphamine, 14-cinnamoyloxycodeinone, ciprefadol, ciramadol, clonitazene, codeine, codeine-6-glucuronide, codeinone, codoxime, conorfone, DADLE, DAMGO, dermorphin, desmethylclozapine, desmethylprodine, O-desmethyltramadol, desomorphine, dextromoramide, dextropropoxyphene, diacetyldihydromorphine, diampromide, dibenzoylmorphine, dibutyrylmorphine, diethylthiambutene, difenoxin, dihydrocodeine, dihydroetorphine, dihydromorphine, dimenoxadol, dimepheptanol, dimethylaminopivalophenone, dimethylthiambutene, dioxaphetyl butyrate, diphenoxylate, dipipanone, dipropanoylmorphine, doxpicomine, DPI-3290, drotebanol, eluxadoline, 6, 14-endoethenotetrahydrooripavine, endomorphin, endomorphin-1, endomorphin-2, β-Endorphin, eseroline, ethoheptazine, 14-ethoxymetopon, ethylmethylthiambutene, ethylmorphine, etonitazene, etorphine, etoxeridine, fentanyl, 4-fluorobutyrfentanyl, 4-fluoropethidine, furanylfentanyl, furethidine, hemorphin-4, heroin, heterocodeine, hodgkinsine, hydrocodone, hydromorphinol, hydromorphone, 14-hydroxydihydrocodeine, 7-hydroxymitragynine, hydroxypethidine, IBNtxA, IC-26, 1-iodomorphine, isomethadone, ketamine, ketobemidone, lefetamine, levacetylmethadol, levallorphan, levomethadone, levomethorphan, levophenacylmorphan, levorphanol, lofentanil, loperamide, loperamide/simethicone, meprodine, metethoheptazine, methadone, metheptazine, 4-methoxybutyrfentanyl, 14-methoxydihydromorphinone, 14-methoxymetopon, α-methylacetylfentanyl, 3-methylbutyrfentanyl, n-methylcarfentanil, methyldesorphine, methyldihydromorphine, 6-methylenedihydrodesoxymorphine, 3-methylfentanyl, α-methylfentanyl, β-methylfentanyl, methylketobemidone, 3-methylthiofentanyl, metofoline, metopon, mirfentanil, mitragynine, mitragynine pseudoindoxyl, 6-monoacetylmorphine, morpheridine, morphine, morphine-6-glucuronide, morphine-n-oxide, morphinone, MR-2096, MT-45, myrophine, nalmexone, naltalimide, nicocodeine, nicodicodeine, nicomorphine, noracymethadol, norbuprenorphine, norketamine, norlevorphanol, normethadone, noroxymorphone, ocfentanil, ohmefentanyl, oliceridine, oxpheneridine, oxycodone, oxymorphazone, oxymorphol, oxymorphone, oxytrex, parafluorofentanyl, pentamorphone, PEPAP, pericine, pethidine, phenadoxone, phenampromide, phenaridine, phenazocine, pheneridine, N-phenethyl-14-ethoxymetopon, N-phenethylnordesomorphine, N-phenethylnormorphine, phenomorphan, phenoperidine, 4-phenylfentanyl, 14-phenylpropoxymetopon, picenadol, piminodine, opium, thebaine, naltrexone, naloxone, nalmefene, samidorphan, nalorphine, nalorphine dinicotinate, nalodeine, dezocine, eptazocine, butorphanol, levorphanol, nalbuphine, pentazocine, phenazocine, cyprodime, naltrindole, norbinaltorphimine, J-113,397, AT-076, papaverine, noscapine, and zyklophin.

In certain embodiments, more than one type of agent may be administered at the same or different times to treat the same or different condition. The effective amount of a given agent may vary somewhat from subject to subject, and may depend upon factors such as, but not limited to, the age and condition of the subject, the form of the agent, the route and method of delivery, etc., as noted above. Dosages may be determined in accordance with routine pharmacological procedures known to those skilled in the art.

Depending on the particular agent(s) administered to a subject, the agent(s) may be administered to a subject using any convenient means. Thus, a pharmacological agent may be incorporated into a variety of formulations for administration to a subject. A pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the one or more pharmacological agents and other optional ingredients of the subject pharmacological agent compositions in that a pharmaceutically acceptable carrier may be combined with the pharmacological agent(s) without eliminating the biological or therapeutically effective activity of the one or more pharmacological agents, and is suitable for use in subjects as provided herein without undue adverse side effects (such as toxicity, irritation, allergic response, and death). Side effects are "undue" when their risk outweighs the benefit provided by the pharmaceutical agent. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agents employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperitoneal, transdermal, intracheal, intravaginal, endocervical, intrathecal, intranasal, intravesicular, in or on the eye, in the ear canal, etc., administration. In certain embodiments, one or more pharmacological agents may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

Embodiments may include pharmacological agent formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological agent formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an aqueous or non-aqueous liquid; or as an oil-in-water or water-in-oil emulsion. Such pharmacological agent formulations may be prepared by any suitable method of pharmacy which includes, but is not limited to, bringing into association the active pharmacological agent and a suitable carrier (which may contain one or more optional ingredients as noted above). For example, pharmacological agent formulations for use with the subject invention may be prepared by uniformly and intimately admixing the active pharmacological agent(s) with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

Pharmacological agents may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include one or more pharmacological agent(s) made into suppositories by mixing with a variety of bases such as emulsifying bases or water-soluble bases. Pharmacological agents may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include at least one pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, the one or more pharmacological agent agents may be utilized in aerosol formulation or an analogous formulation to be administered via inhalation or analogous means. The one or more pharmacological agents employed in the practice of the present invention may be formulated into pressurized acceptable propellants such as dichlorodifluoromethane, propane, nitrogen and the like.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient.

Pharmacological agents may be provided as a salt and may be formed with one or more acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological agents may be administered parenterally, such as intravenous (IV) administration, and may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological agent formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

Pharmacological agents may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include one or more pharmacological agents administered as liposomal formulations of the pharmacological agents. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

A pharmaceutical composition of the subject invention may optionally contain, in addition to a pharmacological agent, at least one other therapeutic agent useful in the treatment of a condition. Such other compounds may be of any class of drug or pharmaceutical agent, including but not limited to antibiotics, anti-parasitic agents, antifungal agents, anti-viral agents, anti-tumor agents, anti-neurodegenerative agents and anti-psychotic agents. When administered with anti-parasitic, anti-bacterial, anti-fungal, anti-tumor, anti-viral agents, anti-neurodegenerative, and anti-psychotic agents and the like, pharmacological agents may be administered by any method and route of administration suitable to the treatment of the condition, typically as pharmaceutical compositions.

Pharmacological agents may include compositions that may be prepared from water-insoluble compounds, or salts thereof, such as aqueous base emulsions. In such embodiments, the pharmacological agent composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agents, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use. Pharmacological agent compositions for use in practicing the subject methods may be lyophilized using techniques well known in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags.

In certain embodiments, a pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological agent formulations include, but are not limited to, formulations that include one or more active pharmacological agents and physiological saline solution (optionally including other typical ingredients such as other active agents and buffers).

As noted above, in pharmaceutical dosage forms, agents may be administered alone or with an appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent calculated in an amount sufficient to produce the desired effect in association with a pharmaceutically acceptable diluent, carrier or vehicle. The specifications for the unit dosage forms of pharmacological agents of the present invention depend on, for example, the particular pharmacological agent(s) employed and the effect to be achieved, the pharmacodynamics associated with the particular pharmacological agent(s) in the subject, etc.

Embodiments include administering an effective amount of a first agent and an effective amount of a second agent. For example, embodiments may include administering a first agent and a second agent to provide an enhanced therapeutic effect. By "enhanced therapeutic effect" is meant that at least the desired outcome occurs more quickly and/or is of greater magnitude with a combination of the pharmacological agents, as compared to the same doses of each component given alone; or that doses of one or all component(s) are below what would otherwise be a minimum effective dose (a "sub-MED").

Any two pharmacological agents may be given in close enough temporal proximity to allow their individual therapeutic effects to overlap. For example, embodiments of the subject invention include the co-timely administration of a first and second agent, where "co-timely" is meant administration of a second pharmacological agent while a first pharmacological agent is still present in a subject in a therapeutically effective amount. It is to be understood that in some instances this will require sequential administration. Alternatively, multiple routes of administration may be employed, e.g., intravenous or subcutaneous injection combined with oral administration, and the like.

Embodiments also include pharmaceutical compositions in unit dosage forms that are useful which contain more than one type of pharmacological agent. In other words, a single agent administration entity may include two or more pharmacological agents. For example, a single tablet, capsule, dragee, trocheem suppository, syringe, and the like, combining two or more pharmacological agents would be a unit dosage form. The therapeutic agents present in a unit dosage form may be present in amounts such that, upon administration of one or more unit doses of the composition, a subject experiences, e.g., a longer lasting efficacy than with the administration of either agent alone and/or greater magnitude and/or quicker lowering of action. Such compositions may be included as part of a therapeutic package in which one or more unit doses are placed in a finished pharmaceutical container. Labeling may be included to provide directions for using the composition according to the invention.

The actual amounts of each agent in such single unit dosage forms may vary according to the specific compositions being utilized, the particular compositions formulated, the mode of application, the particular route of administration, and the like, where dosages for a given subject may be determined using conventional considerations, e.g., by customary comparison of the differential activities of the subject compositions and of a known agent, or by means of an appropriate, conventional pharmacological protocol.

As noted above, certain embodiments include employing electrical neuromodulation in a manner effective to treat a subject for a dermatological condition, according to the subject methods. Electrical neuromodulation systems and devices that may be employed in embodiments of the invention include those systems/devices that enhance or suppress the activity of the nervous system through focused delivery of electrical, optical, magnetic, thermal or chemical signals and stimulation to various areas of the brain, spinal cord, or peripheral nerves, among other locations.

Any suitable area may be targeted for electrical modulation. Areas that may be targeted include, but are not limited to, pre- and post ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency, e.g., to increase or decrease the sensitivity of a synapse and include modulating presynaptic neurons.

As such, areas which may be targeted with electrical energy include, but are not limited to, pre- and post ganglionic nerve fibers, ganglionic structures, efferent and afferent nerve fibers, the hypothalamus, receptors any receptor described herein, afferent autonomic nerves (sympathetic and parasympathetic). Embodiments include receptors of the hypothalamus, including hormonal receptors on the hypothalamus. In certain embodiments, a given nerve fiber or the like may be targeted for electrical modulation in more than one area of the nerve fiber. Targeted areas of the nervous system which may be targeted in accordance with the subject invention include, but are not limited to, vagus nerve, optic ganglion, and sphenopalatine ganglion, internal carotid nerve and plexus, middle and superior cervical sympathetic ganglion; vertebral ganglion; cervicothoracic ganglion; sympathetic trunk; cervical cardiac nerves; cardiac plexus; thoracic aortic plexus; celiac ganglion; celiac trunk and plexus; superior mesenteric ganglion; superior mesenteric artery and plexus; intermesenteric plexus; inferior mesenteric ganglion; inferior mesenteric artery and plexus; superior hypogastric plexus; hypogastric nerves; vesical plexus; thoracic cardiac nerves; sympathetic trunk; 6th thoracic sympathetic ganglion; gray and white rami communicantes; greater, lesser and least splanchnic nerves; aorticorenal ganglion; lumbar splanchnic nerves; gray rami communicantes and sacral splanchnic nerves; and the like, or a combination of two or more of the above.

A number of different devices may be employed in accordance with the subject invention. For example, device and systems for applying electrical energy to a subject and which may be adapted for use in the subject invention are described, e.g., in U.S. Pat. Nos. 7,149,574; 7,363,076 and 7,738,952; the disclosures of the US patent applications are herein incorporated by reference.

Such devices may be positioned directly on a targeted area, e.g., positioned below the skin of a subject directly on or adjacent a portion of the nervous system (e.g., one or more nerve fibers) such as an implantable device, or may be an external device (i.e., some or all of the device may be external to the subject). Such devices may be referred to as body-associated electrical stimulation devices, and may be topically located or implanted. In accordance with the subject invention, one or more electrodes or electrical contacts may be positioned directly on or adjacent a targeted area, where the one or more electrodes may be surgically implanted, e.g., directly on or adjacent a targeted nerve fiber of a subject. In certain embodiments, an immunomodulator such as a steroid or the like, may be incorporated into a surface contacting area of a device, e.g., to minimize inflammation of the targeted site.

An electric energy applying device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of an exemplary electrode suitable for use in the subject methods is applicable to other electrodes that may be employed.

The electrode employed in the subject invention is controllable to provide output signals that may be varied in voltage, frequency, pulse width, current and intensity. The electrode may be one that provides both positive and negative current flow from the electrode and/or may be capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output may be provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed).

A controller or programmer may also be coupled with an electric energy applying device. The programmer is typically one or more microprocessors under the control of a suitable software program. Other components of the programmer will be apparent to those of skill in the art, e.g., analog to digital converter, etc. The electric energy applying device may be pre-programmed for desired parameters. In certain embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

FIG. 1 shows an exemplary embodiment of an electric energy applying device 100. Device 100 may be implanted in a suitable position of a subject's body 10. One or more leads 23 are shown positioned to stimulatory or inhibitory electrical energy. Device 100 include energy source 14 which may take the form of a modified signal generator, Model 7424 manufactured by Medtronic, Inc. under the trademark Intrel II. Lead 23 may take the form of any suitable lead, such as any of the leads that are sold with the Model 7427 and is coupled to energy source 14 by one or more conventional conductors 16 and 18. Lead 23 may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed parameter or condition of a subject. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

As shown in FIG. 1, the distal end of lead 23 terminates in one or more delivery elements such as stimulation electrodes which may be implanted using conventional surgical techniques. The type of treatment that is desired determines the location of the electrodes. Any number of electrodes may be used for various applications. Each of the electrodes may be individually connected to energy source 14 through lead 23 and conductors 16 and 18. Lead 23 may be surgically implanted either by a laminotomy or by a needle.

Energy source or signal generator 14 may be programmed to provide a predetermined stimulation (or inhibition) dosage in terms of pulse amplitude, pulse width, pulse frequency, or duty cycle. As shown, a programmer 20 may be utilized to provide stimulation (or inhibition) parameters to the delivery device via any suitable technology, e.g., using telemetry and the like. For example, in using telemetry, programmer 20 may be coupled to an antenna 24 via conductor 22. In certain embodiments, the programmer may be positioned, e.g., implanted, inside body 10. For example, in certain embodiments the programmer may be integrated with the energy source, electrode, etc., for example as a single unit.

Device 100 may optionally include one or more sensors to provide closed-loop feedback control of the treatment and/or electrode positioning. One or more sensors (not shown) may be attached to or implanted into a portion of a subject's body suitable for detecting a physical and/or chemical indicator of the subject. For example, sensing feedback may be accomplished, e.g., by a mechanical measure within a lead or an ultrasound or other sensor to provide information about the treatment parameters, lead positioning, LTP, etc.

Operative placement of a suitable electric energy applying device may be accomplished using any suitable technique. An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical. For exemplary purposes only, the subject method will be described using a fluoroscope, where such is in no way intended to limit the scope of the invention. The subject is placed in a suitable position for access e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is positioned the stylet is withdrawn from the electrode introducer needle. Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control the electrode may be surgically implanted in the desired region by procedures known in the art, such as have been applied in surgical neuromodulation therapies used to treat Parkinson's disease.

In certain embodiments of the subject invention, an electrode may be utilized which, instead of or in addition to delivering electric impulses to at least a portion of the autonomic nervous system, delivers a pharmacological agent to at least a portion of the autonomic nervous system. For example, an electrode may be used that has a small port at its tip which is connected to a reservoir or pump containing a pharmacological agent. The pharmacological agent delivery electrode may be implanted using an analogous procedure as that described above for the autonomic system modulating-electrode. In certain embodiments the reservoir or pump may also be implanted in the subject's body, analogous to that described above for the electrical impulse generator. The pharmacological agent delivery electrode may be controllable such that the amount of pharmacological agent delivered, the rate at which the pharmacological agent may be delivered, and the time period over which the pharmacological agent is delivered may be adjusted.

In embodiments in which electrical energy is used, any suitable protocol may be used, where certain protocols include using an electric energy applying device to deliver a suitable amount of electrical energy to a subject. Once an electric energy applying device is positioned in a suitable position on or about one or more targeted areas electrical energy is applied thereto for a period of time sufficient to provide the desired effect. This period of time will vary depending on the area (e.g., the nerve fiber) being treated, the condition being treated, etc. Certain embodiments include simultaneously monitoring (i.e., in "real time") the aspect of the nervous system such that a given nerve fiber may be electrically stimulated (or electrically inhibited) until the desired result is observed. Still further, in many embodiments once the desired result is achieved, a targeted area may be repeatedly electrically stimulated (or inhibited) one or more times to maintain the desired state such that the subject methods may be repeated one or more times, i.e., the subject methods include chronically applying electrical energy to a subject, such as chronically applying electrical energy to one or more nerve fibers. For example, in certain embodiments electrical stimulation (e.g., intermittent mild electrical pulses) may be delivered to a given area of the nervous system, twenty-four hours a day for a period of days, weeks, months, or even years in certain embodiments.

During the period of time that electrical energy is applied to a given area, the electrical energy may be substantially continuous, including continuous or intermittent (i.e., pulsed or periodic), where in many embodiments the electrical energy is in the form of electrical pulses. In other words, in certain embodiments electrical energy may be given continuously during the above-described period of time and in certain embodiments electrical energy may be given to an area in a pulsed or intermittent manner during the period of time described above. In accordance with the subject methods to apply electrical energy to a subject, once operatively positioned the electric energy applying device is activated to provide an electrical signal to the targeted area in a manner effective to practice the subject methods.

In practicing the subject methods, activation of the electric energy applying device directly applies the electrical output of the device, i.e., electrical impulses, to the targeted area. The exact parameters of the applied electrical energy may vary depending on the particular subject, condition being treated, etc. For example, an electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar.

For example, to stimulate a targeted area, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

In certain embodiments, a control feedback loop is provided. For example, during or following a particular electric energy applying protocol, a biological aspect of a subject may be monitored, e.g., by sensing conduction in a neuronal system, e.g., in a particular electrically stimulated nerve fiber, or by any suitable method. For example, a sensor suitable for detecting nerve cell or axon activity may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if a predetermined detection criteria is not detected the same or a different stimulus protocol may be performed and may be automatically initiated under the control of a controller. For example, in those instances where a different protocol is performed, one or more of the electrical energy applying parameters may be modified, e.g., the pulse width may be increased, or the like, in the second protocol.

A variety of different dermatological conditions may be treated in accordance with methods of invention. As summarized above, dermatological conditions are diseases, disorders, symptoms, etc. involving the skin. A non-limiting list of dermatological conditions include, but are not limited to: Acneiform eruptions (e.g., eruptions caused by changes in the pilosebaceous unit), such as but not limited to: Acne aestivalis, Acne conglobata, Acne cosmetica (cosmetic acne), Acne fulminans (acute febrile ulcerative acne), Acne keloidalis nuchae (acne keloidalis, dermatitis papillaris capillitii, folliculitis keloidalis, folliculitis keloidis nuchae, nuchal keloid acne), Adult forehead with scattered red pimples, Acne vulgaris, Acne mechanica, Acne medicamentosa, Acne miliaris necrotica (acne varioliformis), Acne vulgaris (acne simplex), Acne with facial edema (solid facial edema), Blepharophyma, Erythrotelangiectatic rosacea (erythematotelangiectatic rosacea, vascular rosacea). Excoriated acne (acne excoriée des jeunes filles, Picker's acne), Glandular rosacea, Gnathophyma, Gram-negative rosacea, Granulomatous facial dermatitis, Adult male with a large, red, bulbous nose, Rhinophyma, Granulomatous perioral dermatitis, Halogen acne, Hidradenitis suppurativa (acne inversa, pyoderma fistulans significa, Verneuil's disease), Idiopathic facial aseptic granuloma, Infantile acne, Lupoid rosacea (granulomatous rosacea, micropapular tuberculid, rosacea-like tuberculid of Lewandowsky), Lupus miliaris disseminatus faciei, Metophyma, Neonatal acne (acne infantum, acne neonatorum, neonatal cephalic pustulosis), Occupational acne, Oil acne, Ocular rosacea (ophthalmic rosacea, ophthalmorosacea), Otophyma, Periorificial dermatitis, Persistent edema of rosacea (chronic upper facial erythematous edema, Morbihan's disease, rosaceous lymphedema), Phymatous rosacea, Pomade acne, Papulopustular rosacea (inflammatory rosacea), Perifolliculitis capitis abscedens et suffodiens (dissecting cellulitis of the scalp, dissecting folliculitis, perifolliculitis capitis abscedens et suffodiens of Hoffman), Perioral dermatitis, Periorbital dermatitis (periocular dermatitis), Pyoderma faciale (rosacea fulminans), Rhinophyma, Rosacea (acne rosacea), Rosacea conglobata, Synovitis-acne-pustulosis-hyperostosis-osteomyelitis syndrome (SAPHO syndrome), Steroid rosacea, Tar acne, Tropical acne, etc.; Autoinflammatory syndromes (e.g., inherited disorders characterized by bouts of inflammatory skin lesions and periodic fevers), such as but not limited to: Blau syndrome, Chronic infantile neurologic cutaneous and articular syndrome, Familial cold urticaria (familial cold autoinflammatory syndrome), Familial Mediterranean fever Hyper-IgD syndrome, Majeed syndrome, Muckle-Wells syndrome, TNF receptor associated periodic syndrome (familial Hibernian fever, TRAPS, tumor necrosis factor receptor associated periodic syndrome), etc.; Chronic blistering (cutaneous conditions have a prolonged course and present with vesicles and bullae), such as but not limited to Adult linear IgA disease, Bullous pemphigoid, Childhood linear IgA disease (chronic bullous disease of childhood), Cicatricial pemphigoid (benign mucosal pemphigoid, benign mucous membrane pemphigoid, ocular pemphigus, scarring pemphigoid), Dermatitis herpetiformis (Duhring disease), Endemic pemphigus (endemic pemphigus foliaceus, fogo selvagem), Epidermolysis bullosa acquisita, Grover's disease (benign papular acantholytic dermatosis, persistent acantholytic dermatosis, transient acantholytic dermatosis), Adult chest and abdomen with many red skin lesions, IgA pemphigus Intraepidermal neutrophilic IgA dermatosis, Localized cicatricial pemphigoid (Brunsting-Perry cicatricial pemphigoid), Paraneoplastic pemphigus, Pemphigus erythematosus (Senear-Usher syndrome), Pemphigus foliaceus, Pemphigus herpetiformis (acantholytic herpetiform dermatitis, herpetiform pemphigus, mixed bullous disease, pemphigus controlled by sulfapyridine), Pemphigoid nodularis, Pemphigus vegetans, Pemphigus vegetans of Hallopeau, Pemphigus vegetans of Neumann, Pemphigus vulgaris, Vesicular pemphigoid, Vulvar childhood pemphigoid, etc.; Conditions of the mucous membranes (conditions involving the moist linings of the eyes, nose, mouth, genitals, and anus), such as but not limited to, Acatalasia (acatalasemia, Takahara's disease), Acquired dyskeratotic leukoplakia, Actinic cheilitis (actinic cheilosis), Acute necrotizing ulcerative gingivitis (acute membranous gingivitis, acute necrotizing ulcerative gingivostomatitis, fusospirillary gingivitis, fusospirillosis, fusospirochetal gingivitis, necrotizing gingivitis, phagedenic gingivitis, trench mouth, ulcerative gingivitis, Vincent gingivitis, Vincent infection, Vincent stomatitis, Vincent's disease), Allergic contact cheilitis, Adult tongue with a strikingly black top, Angina bullosa haemorrhagica, Angular cheilitis (perlèche), Behçet's disease (Behçet's syndrome, oculo-oral-genital syndrome), Black hairy tongue (hairy tongue, lingua villosa nigra), Caviar tongue, Cheilitis exfoliativa, Cheilitis glandularis, Cheilitis granulomatosa (granulomatous cheilitis, orofacial granulomatosis), Cutaneous sinus of dental origin (dental sinus), Cyclic neutropenia, Desquamative gingivitis, Drug-induced ulcer of the lip, Epidermization of the lip, Epulis, Epulis fissuratum (granuloma fissuratum), Eruptive lingual papillitis, Erythroplakia (erythroplasia), Fissured tongue (furrowed tongue, lingua plicata, plicated tongue, scrotal tongue), Geographic tongue (benign migratory glossitis, benign migratory stomatitis, glossitis areata exfoliativa, glossitis areata migrans, lingua geographica, stomatitis areata migrans, transitory benign plaques of the tongue), Gingival fibroma, Gingival hypertrophy, Hairy leukoplakia (oral hairy leukoplakia), Intraoral dental sinus, Linea alba, Leukoplakia, Leukoplakia with tylosis and esophageal carcinoma, Major aphthous ulcer (periadenitis mucosa necrotica recurrens), Median rhomboid glossitis (central papillary atrophy), Melanocytic oral lesion, Melkersson-Rosenthal syndrome, Morsicatio buccarum (chronic cheek biting, chronic cheek chewing), Mucosal squamous cell carcinoma, Mucous cyst of the oral mucosa (mucocele), Nagayama's spots, Oral Crohn's disease, Oral florid papillomatosis, Oral melanosis, Osseous choristoma of the tongue, Peripheral ameloblastoma, Plasma cell cheilitis (plasma cell gingivitis, plasma cell orificial mucositi), Plasmoacanthoma, Proliferative verrucous leukoplakia, Pyogenic granuloma (eruptive hemangioma, granulation tissue-type hemangioma, granuloma gravidarum, lobular capillary hemangioma, pregnancy tumor, tumor of pregnancy), A solitary papule of inflamed vascular granulation tissue on the index finger of an adult, Pyogenic granuloma, Pyostomatitis vegetans, Recurrent aphthous stomatitis (aphthosis, canker sores, recurrent oral aphthae), Recurrent intraoral herpes simplex infection, Smooth tongue (atrophic glossitis, bald tongue, hunter glossitis, moeller), Stomatitis nicotina (nicotine stomatitis, smoker's keratosis, smoker's patches), Torus palatinus, Trumpeter's wart, Vestibular papillomatosis, White sponge nevus (white sponge nevus of Cannon); Conditions of the skin appendages (conditions affecting the glands of the skin, hair, nails, and arrector pili muscles), such as but not limited to, Acne necrotica, Acquired generalized hypertrichosis (acquired hypertrichosis lanuginosa, hypertrichosis lanuginosa acquisita), Acquired perforating dermatosis (acquired perforating collagenosis), Acrokeratosis paraneoplastica of Bazex (acrokeratosis neoplastica, Bazex syndrome), Acroosteolysis, Acute paronychia, Circular coin-sized bare patch on the back of a person's scalp, Alopecia areata, Alopecia areata, Alopecia neoplastica, Anagen effluvium, Androgenic alopecia (androgenetic alopecia), Anhidrosis (hypohidrosis), Anonychia, Apparent leukonychia, Beau's lines, Blue nails, Bromidrosis (apocrine bromhidrosis, fetid sweat, malodorous sweating, osmidrosis), Bubble hair deformity, Central centrifugal cicatricial alopecia (follicular degeneration syndrome, pseudopelade of the central scalp), Chevron nail (herringbone nail), Chromhidrosis (colored sweat), Chronic paronychia, Cicatricial alopecia, Clubbing (drumstick fingers, Hippocratic fingers, watch-glass nails), Congenital onychodysplasia of the index fingers, Disseminate and recurrent infundibulofolliculitis, Erosive pustular dermatitis of the scalp (erosive pustular dermatosis of the scalp), Erythromelanosis follicularis faciei et colli, Folliculitis decalvans, Folliculitis nares perforans, Fox-Fordyce disease, Frontal fibrosing alopecia, Generalized congenital hypertrichosis (congenital hypertrichosis lanuginosa), Generalized hyperhidrosis, Graham-Little syndrome, Granulosis rubra nasi, Big toe with most of the toenail missing; only the nail's root is present, Nail-patella syndrome, Green nails, Gustatory hyperhidrosis, Hair casts (pseudonits), Hair follicle nevus (vellus hamartoma), Hairy palms and soles, Half and half nails (Lindsay's nails), Hangnail, Hapalonychia, Hematidrosis, Hirsutism, Hook nail, Hot comb alopecia, Hypertrichosis cubiti (hairy elbow syndrome), Hypertrichosis simplex of the scalp, Intermittent hair-follicle dystrophy, Keratosis pilaris atrophicans, Kinking hair (acquired progressive kinking), Koenen's tumor (Koenen's periungual fibroma, periungual fibroma), Koilonychia (spoon nails), Kyrle disease, Leukonychia (white nails), Lichen planopilaris (acuminatus, follicular lichen planus, lichen planus follicularis, peripilaris), Lichen planus of the nails, Lichen spinulosus (keratosis spinulosa), Lipedematous alopecia (lipedematous scalp), Localized acquired hypertrichosis, Localized congenital hypertrichosis, Longitudinal erythronychia, Longitudinal melanonychia, Loose anagen syndrome (loose anagen hair syndrome), Lupus erythematosus, Madarosis, Malalignment of the nail plate, Male-pattern baldness, Marie-Unna hereditary hypotrichosis (Marie-Unna hypotrichosis), Median nail dystrophy (dystrophia unguis mediana canaliformis, median canaliform dystrophy of Heller, solenonychia), Mees' lines, Melanonychia, Menkes kinky hair syndrome (kinky hair disease, Menkes disease), Monilethrix (beaded hair), Muehrcke's nails (Muehrcke's lines), Multiple, dystrophic, irregular, shortened fingernails, Onychotillomania, Nail-patella syndrome (Fong syndrome, hereditary osteoonychodysplasia, HOOD syndrome), Neoplasms of the nailbed, Nevoid hypertrichosis, Noncicatricial alopecia, Onychauxis, Onychoatrophy, Onychocryptosis (ingrown nail, unguis incarnatus), Onychogryphosis (ram's horn nails), Onycholysis, Onychomadesis, Onychomatricoma, Onychophagia (nail biting), Onychophosis, Onychoptosis defluvium (alopecia unguium), Onychorrhexis (brittle nails), Onychoschizia, Onychotillomania, Ophiasis, Palmoplantar hyperhidrosis (emotional hyperhidrosis), Parakeratosis pustulosa, Patterned acquired hypertrichosis, Perforating folliculitis, Pili annulati (ringed hair), Pili bifurcati, Pili multigemini, Pili pseudoannulati (pseudo pili annulati), Pili torti (twisted hairs), Pincer nails (omega nails, trumpet nails), Pityriasis amiantacea (tinea amiantacea), Platonychia, Plica neuropathica (felted hair), Plummer's nail, Prepubertal hypertrichosis, Pressure alopecia (postoperative alopecia, pressure-induced alopecia), Pseudofolliculitis barbae (barber's itch, folliculitis barbae traumatica, razor bumps, scarring pseudofolliculitis of the beard, shave bumps), Pseudopelade of Brocq (alopecia cicatrisata), Psoriatic nails, Pterygium inversum unguis (pterygium inversus unguis, ventral pterygium), Pterygium unguis (dorsal pterygium), Purpura of the nail bed, Racquet nail (brachyonychia, nail en raquette, racquet thumb), Recurrent palmoplantar hidradenitis (idiopathic palmoplantar hidradenitis, idiopathic plantar hidradenitis, painful plantar erythema, palmoplantar eccrine hidradenitis, plantar panniculitis), Red lunulae, Ross' syndrome, Rubinstein-Taybi syndrome, Setleis syndrome, Shell nail syndrome, Short anagen syndrome, Splinter hemorrhage, Small, linear, blue-black areas of discoloration beneath the nail plate of an adult finger, Splinter hemorrhage, Spotted lunulae, Staining of the nail plate, Stippled nails, Subungual hematoma, Telogen effluvium, Terry's nails, Traction alopecia, Traumatic alopecia, Traumatic anserine folliculosis, Triangular alopecia (temporal alopecia, temporal triangular alopecia), Trichomegaly, Trichomycosis axillaris, Trichorrhexis invaginata (bamboo hair), Trichorrhexis nodosa, Trichostasis spinulosa, Tufted folliculitis, Tumor alopecia, Twenty-nail dystrophy (sandpapered nails, trachyonychia), Uncombable hair syndrome (cheveux incoiffable, pili trianguli et canaliculi, spun-glass hair), Wooly hair nevus (woolly hair nevus), X-linked hypertrichosis; Conditions of the subcutaneous fat (conditions affecting the layer of adipose tissue that lies between the dermis and underlying fascia), such as but not limited to: Acquired generalized lipodystrophy (Lawrence syndrome, Lawrence-Seip syndrome), Adiposis dolorosa (Dercum's disease)

Alpha-1 antitrypsin deficiency panniculitis (alpha1-protease deficiency panniculitis, alpha1-proteinase deficiency panniculitis), Atrophic connective tissue panniculitis Barraquer-Simons syndrome (acquired partial lipodystrophy, cephalothoracic lipodystrophy, progressive lipodystrophy), Benign symmetric lipomatosis (benign symmetric lipomatosis of Launois-Bensaude, Madelung's disease), Centrifugal abdominal lipodystrophy (centrifugal lipodystrophy, lipodystrophia centrifugalis abdominalis infantalis), Chronic erythema nodosum (erythema nodosum migrans, subacute migratory panniculitis of Vilanova and Pinol, subacute nodular migratory panniculitis), Dark area of skin, reminiscent of a bruise, on the inner ankle of an adult, Chronic erythema nodosum, Cold panniculitis (popsicle panniculitis), Congenital generalized lipodystrophy (Berardinelli-Seip syndrome), Cytophagic histiocytic panniculitis, Drug-induced lipodystrophy, Factitial panniculitis, Familial partial lipodystrophy (Kobberling-Dunnigan syndrome), Gouty panniculitis, Hemihyperplasia-multiple lipomatosis syndrome, HIV-associated lipodystrophy, Involutional lipoatrophy, Lipoatrophia annularis (Ferreira-Marques lipoatrophia), Lipoatrophia semicircularis (semicircular lipoatrophy), Lipodermatosclerosis (chronic panniculitis with lipomembranous changes, hypodermitis sclerodermiformis, sclerosing panniculitis, stasis panniculitis), Lipohypertrophy, Localized lipodystrophy, Neutrophilic lobular panniculitis, Nodular vasculitis, Nonprogressive late-onset linear hemifacial lipoatrophy, Pancreatic panniculitis (enzymatic panniculitis, pancreatic fat necrosis, subcutaneous fat necrosis), Poland's syndrome, Post-steroid panniculitis, Sclerema neonatorum, Sclerosing lipogranuloma (paraffinoma), Septal panniculitis, Subcutaneous fat necrosis of the newborn, Traumatic panniculitis, Tumor lysis syndrome, Weber-Christian disease (relapsing febrile nonsuppurative panniculitis); Cutaneous congenital anomalies (disorders that result from faulty morphogenesis, the biological process that forms the shape of a human body), such as but not limited to Accessory nail of the fifth toe, Accessory tragus (ear tag, preauricular appendage, preauricular tag), Amniotic band syndrome (ADAM complex, amniotic band sequence, congenital constriction bands, pseudoainhum), Aplasia cutis congenita (cutis aplasia, congenital absence of skin, congenital scars), Arteriovenous fistula, Benign neonatal hemangiomatosis, Branchial cyst (branchial cleft cyst), Bronchogenic cyst, Capillary hemangioma (infantile hemangioma, nevus maternus, strawberry hemangioma, strawberry nevus), Cavernous venous malformation, Congenital cartilaginous rest of the neck (cervical accessory tragus, wattle), Congenital erosive and vesicular dermatosis, Congenital hypertrophy of the lateral fold of the hallux, Congenital lip pit (congenital sinus of the lower lip, lip sinus, midline sinus of the upper lip), Congenital malformations of the dermatoglyphs, Congenital smooth muscle hamartoma, Cystic lymphatic malformation, Dermoid cyst, Diffuse neonatal hemangiomatosis, Encephalocele, Focal facial dermal dysplasia, Hutchinson's teeth, Hyperkeratotic cutaneous capillary-venous malformation, Intrauterine epidermal necrosis, Limb-mammary syndrome, Lowry-MacLean syndrome, Macrocheilia, Macrocystic lymphatic malformation, Malignant pilomatricoma (pilomatrical carcinoma, pilomatrix carcinoma), Maternal autoimmune bullous disease, Median raphe cyst, Melanotic neuroectodermal tumor of infancy, Membranous aplasia cutis, Microcystic lymphatic malformation, Midline cervical cleft, Mongolian spot (congenital dermal melanocytosis, dermal melanocytosis), Several light blue patches of skin distributed over a child's lower back and buttock, Mongolian spot, Mulberry molar, Nager acrofacial dysostosis, Nasal glioma (brain-like heterotopia, cephalic brain-like heterotopia, glial hamartoma, heterotopic neuroglial tissue, nasal cerebral heterotopia, nasal heterotopic brain tissue), Nasolacrimal duct cyst, Nevus psiloliparus, Non-involuting congenital hemangioma, Omphalomesenteric duct cyst (omphalomesenteric duct remnant, vitelline cyst), PELVIS syndrome, Pilomatricoma (calcifying epithelioma of Malherbe, Malherbe calcifying epithelioma, pilomatrixoma), Poland anomaly, Posterior fossa malformations-hemangiomas-arterial anomalies-cardiac defects-eye abnormalities-sternal cleft and supraumbilical raphe syndrome (PHACE association, PHACES syndrome), Preauricular sinus and cyst (ear pit, congenital auricular fistula, congenital preauricular fistula, preauricular cyst), Rapidly involuting congenital hemangioma (congenital nonprogressive hemangioma), Rosenthal-Kloepfer syndrome, Rudimentary supernumerary digit (rudimentary polydactyly), SACRAL syndrome, Sinus pericranii, Skin dimple (skin fossa), Superficial lymphatic malformation (lymphangioma circumscriptum), Supernumerary nipple (accessory nipple, pseudomamma), Thyroglossal duct cyst, Verrucous vascular malformation (angiokeratoma circumscriptum naeviforme); Connective tissue diseases (diseases caused by a complex array of autoimmune responses that target or affect collagen or ground substance) such as but not limited to Acute cutaneous lupus erythematosus, Atrophoderma of Pasini and Pierini (dyschromic and atrophic variation of scleroderma, morphea plana atrophica, sclérodermie atrophique d'emblée), Calcinosis-Raynaud phenomenon-esophageal dysmotility-sclerodactyly-telangiectasia syndrome (CREST syndrome), Chilblain lupus erythematosus (chilblain lupus erythematosus of Hutchinson), Childhood dermatomyositis, Childhood discoid lupus erythematosus, Childhood systemic lupus erythematosus, Frontal linear scleroderma, Complement deficiency syndromes, Dermatomyositis, Eosinophilia-myalgia syndrome, Frontal linear scleroderma (en coup de sabre, morphea en coup de sabre), Generalized discoid lupus erythematosus, Generalized morphea, Interstitial granulomatous dermatitis, Juvenile rheumatoid arthritis (juvenile idiopathic arthritis, Still's disease), Keloid morphea, Linear atrophoderma of Moulin (Moulin atrophoderma linearis), Linear scleroderma, Localized discoid lupus erythematosus, Localized morphea Lupus erythematosus panniculitis (lupus erythematosus profundus, lupus panniculitis, lupus profundus, subcutaneous lupus erythematosus), Lupus erythematosus-lichen planus overlap syndrome (lichen planus-lupus erythematosus overlap syndrome), Methotrexate-induced papular eruption, Mixed connective tissue disease (Sharp's syndrome, undifferentiated connective tissue disease), Morphea profunda, Morphea-lichen sclerosus et atrophicus overlap, Mouth and genital ulcers with inflamed cartilage syndrome (MAGIC syndrome), Neonatal lupus erythematosus, Nephrogenic systemic fibrosis (nephrogenic fibrosing dermopathy), Nicolau-Balus syndrome, Nodulosis-arthropathy-osteolysis syndrome, Normophosphatemic familial tumoral calcinosis, Palisaded neutrophilic and granulomatous dermatitis, Pansclerotic morphea, Parry-Romberg syndrome (progressive hemifacial atrophy), Progressive systemic sclerosis, Relapsing polychondritis (atrophic polychondritis, systemic chondromalacia), Rheumatoid arthritis, Rheumatoid nodulosis (accelerated rheumatoid nodulosis), Rheumatoid vasculitis, Rowell's syndrome, Scleredema adultorum (Bushke disease, scleredema diabeticorum, scleredema adultorum of Buschke, scleredema of Buschke), Silicosis, Sjögren's syndrome (Mikulicz disease, Sicca syndrome), Subacute cutaneous lupus erythematosus, Systemic lupus erythematosus, Toxic oil syndrome, Tumid lupus erythematosus (lupus erythematosus tumidus), Tuzun syndrome, Verrucous lupus erythematosus (hypertrophic lupus erythematosus), Winchester syndrome; Abnormalities of dermal fibrous and elastic tissue (conditions caused by problems in the regulation of collagen synthesis and/or degradation), such as but not limited to Fuzzy red lines on an abdomen, Striae distensa, Acrodermatitis chronica atrophicans (Herxheimer disease, primary diffuse atrophy), Actinic elastosis (solar elastosis), Anetoderma (anetoderma maculosa, anetoderma maculosa cutis, atrophia maculosa cutis, macular atrophy), Blepharochalasis, Cutis laxa (chalazoderma, dermatochalasia, dermatolysis, dermatomegaly, generalized elastolysis, generalized elastorrhexis, pachydermatocele), Cutis rhomboidalis nuchae, Ehlers-Danlos syndrome (cutis hyperelastica, elastic skin, India rubber skin), Elastosis perforans, serpiginosa, Homocystinuria, Jadassohn-Pellizzari anetoderma, Linear focal elastosis (elastotic striae), Loeys-Dietz syndrome, Marfan syndrome, Occipital horn syndrome, Osteogenesis imperfecta (Lobstein syndrome), Perforating calcific elastosis (localized acquired cutaneous pseudoxanthoma elasticum, perforating periumbilical calcific elastosis, periumbilical perforating pseudoxanthoma elasticum), Pseudoxanthoma elasticum (Grönblad-Strandberg syndrome), Reactive perforating collagenosis, Schweninger-Buzzi anetoderma, Sclerotic fibroma, Striae atrophicans, Striae distensae, Ullrich disease, Verrucous perforating collagenoma, Wrinkly skin syndrome; Dermal and subcutaneous growths, such as but not limited to: Acquired progressive lymphangioma (benign lymphangioendothelioma), Acral arteriolar ectasia, Acral fibrokeratoma (acquired digital fibrokeratoma, acquired periungual fibrokeratoma), Acrochordon (cutaneous papilloma, cutaneous tag, fibroepithelial polyp, fibroma molluscum, fibroma pendulum, papilloma colli, skin tag, soft fibroma, Templeton skin tag), Adenoma sebaceum, Adult type of generalized eruption of cutaneous mastocytosis, African cutaneous Kaposi sarcoma, Multiple, small, blue to red papules on the scrotum, Angiokeratoma of Fordyce, African lymphadenopathic Kaposi sarcoma, Aggressive infantile fibromatosis, AIDS-associated Kaposi sarcoma, Ainhum (bankokerend, dactylolysis spontanea, sukhapakla), Angiofibroma, Angiokeratoma, Angiokeratoma of Fordyce (angiokeratoma of the scrotum and vulva), Angiokeratoma of Mibelli (Mibelli's angiokeratoma, telangiectatic warts), Angioleiomyoma (vascular leiomyoma), Angiolipoleiomyoma, Angiolipoma, Angioma serpiginosum, Angiosarcoma, Aponeurotic fibroma (calcifying aponeurotic fibroma, juvenile aponeurotic fibroma), Atypical fibroxanthoma, Benign lipoblastomatosis (embryonic lipoma), Buschke-Ollendorff syndrome (dermatofibrosis lenticularis disseminata), Capillary aneurysms Carcinoid, Cherry angioma (De Morgan spot, senile angioma), Chondrodermatitis nodularis chronica helicis (chondrodermatitis nodularis helicis), Solitary, pink, dome-shaped papule on the superior helix of an adult, Chondrodermatitis nodularis chronica helicis, Chondroid lipoma, Chordoma, Classic Kaposi sarcoma, Collagenous fibroma (desmoplastic fibroblastoma), Composite hemangioendothelioma, Connective tissue nevus (collagenoma, elastoma, shagreen patch), Cutaneous endometriosis, Cutaneous meningioma (heterotopic meningeal tissue, rudimentary meningocele), Cutaneous myelofibrosis, Cutaneous myxoma, Cutis marmorata telangiectatica congenita (congenital generalized phlebectasia, Van Lohuizen syndrome), Dermal dendrocyte hamartoma, Dermatofibroma (benign fibrous histiocytoma, dermal dendrocytoma, fibrous dermatofibroma, fibrous histiocytoma, fibroma simplex, histiocytoma, nodular subepidermal fibrosis, sclerosing hemangioma), Dermatofibrosarcoma protuberans, Desmoid tumor, Diffuse cutaneous mastocytosis, Diffuse infantile fibromatosis, Dupuytren'sa) contracture (Dupuytren's diathesis, Dupuytren's disease, palmar fibromatosis), Eccrine angiomatous hamartoma, Elastofibroma dorsi, Endovascular papillary angioendothelioma (Dabska tumor, Dabska-type hemangioendothelioma, hobnail hemangioendothelioma, malignant endovascular papillary angioendothelioma, papillary intralymphatic angioendothelioma), Epithelioid cell histiocytoma, Epithelioid hemangioendothelioma, Epithelioid sarcoma, Erythrodermic mastocytosis, Extraskeletal chondroma (chondroma of soft parts), Familial myxovascular fibromas, Fascial hernia, Fibroma of tendon sheath, Fibromatosis colli (sternomastoid tumor of infancy), Fibrous hamartoma of infancy, Fibrous papule of the nose (benign solitary fibrous papule, fibrous papule of the face), Folded skin with scarring (Michelin tire baby syndrome), Fordyce's spot (Fordyce's disease), Ganglion cyst, Ganglioneuroma, Genital leiomyoma (dartoic leiomyoma), Giant cell fibroblastoma, Giant cell tumor of the tendon sheath (giant cell synovioma, localized nodular tenosynovitis, pigmented villonodular synovitis), Glomeruloid hemangioma, Small, raised, skin-colored lesions, Fordyce's spot, Glomus tumor (glomangioma, solid glomus tumor, solitary glomus tumor), Granular cell tumor (Abrikossoff's tumor, Abrikossov's tumor, granular cell myoblastoma, granular cell nerve sheath tumor, granular cell schwannoma), Hamartoma, Hemangiopericytoma, Hemangiosarcoma, Hibernoma (fetal lipoma, lipoma of embryonic fat, lipoma of immature adipose tissue), Hypertrophic scar, Immunosuppression-associated Kaposi sarcoma, Infantile digital fibromatosis (inclusion body fibromatosis, infantile digital myofibroblastoma, Reye tumor), Infantile hemangiopericytoma (congenital hemangiopericytoma), Infantile myofibromatosis (congenital generalized fibromatosis, congenital multicentric fibromatosis), Infantile systemic hyalinosis (juvenile systemic hyalinosis), Intradermal spindle cell lipoma, Intravascular papillary endothelial, hyperplasia (Masson's hemangio-endothelioma vegetant intravasculaire, Masson's lesion, Masson's pseudoangiosarcoma, Masson's tumor, papillary endothelial hyperplasia), Juvenile hyaline fibromatosis (fibromatosis hyalinica multiplex juvenilis, Murray-Puretic-Drescher syndrome), Kaposiform hemangioendothelioma (infantile kaposiform hemangioendothelioma), Kasabach-Merritt syndrome (hemangioma with thrombocytopenia), Keloid (Keloidal scar), Excessive scar tissue along an adult jawline, Keloid, Keratinizing metaplasia, Keratocyst, Klippel-Trenaunay syndrome (angioosteohypertrophy syndrome, hemangiectatic hypertrophy), Knuckle pads (heloderma), Leiomyosarcoma, Lipoma, Liposarcoma (atypical lipoma, atypical lipomatous tumor), Lymphangiectasis (lymphangioma), Lymphangiomatosis, Malignant fibrous histiocytoma, Malignant peripheral nerve sheath tumor (malignant schwannoma, neurofibrosarcoma, neurosarcoma), Mast cell sarcoma, Meningocele, Metastatic carcinoma, Microvenular hemangioma (microcapillary hemangioma), Midline nevus flammeus (angel's kiss, salmon patch), Multifocal lymphangioendotheliomatosis (congenital cutaneovisceral angiomatosis with thrombocytopenia, multifocal, lymphangioendotheliomatosis with thrombocytopenia), Multinucleate cell, angiohistocytoma, Multiple cutaneous and uterine leiomyomatosis syndrome (leiomyomatosis cutis et uteri, multiple leiomyomatosis, Reed's syndrome), Multiple cutaneous leiomyoma (pilar leiomyoma), Neural fibrolipoma, Neuroblastoma (infantile neuroblastoma, neuroepithelioma), Neuroma cutis, Neurothekeoma (bizarre cutaneous neurofibroma, cutaneous lobular neuromyxoma, myxoma of the nerve sheath, myxomatous perineurioma, nerve sheath myxoma), Nevus flammeus (capillary malformation, port-wine stain), Nevus flammeus nuchae (stork bite), Nevus lipomatosus superficialis (nevus lipomatosis of Hoffman and Zurhelle), Nevus oligemicus, Venous lake, Nodular fasciitis (nodular pseudosarcomatous fasciits, pseudosarcomatous fasciitis, subcutaneous pseudosarcomatous fibromatosis), Oral submucous fibrosis, Pachydermodactyly, Palisaded encapsulated neuroma, Paraneoplastic syndrome, Pearly penile papules (hirsuties coronae glandis, hirsutoid papillomas), Peyronie's disease (induratio penis plastica), Phakomatosis pigmentovascularis, Piloleiomyoma, Plantar fibromatosis (Ledderhose's disease), Pleomorphic fibroma, Pleomorphic lipoma, Plexiform fibrohistiocytic tumor, Porokeratotic eccrine ostial and dermal duct nevus, Progressive nodular histiocytoma, Proliferating angioendotheliomatosis, Prominent inferior labial artery, Pseudo-ainhum, Retiform hemangioendothelioma (hobnail hemangioendothelioma), Schwannoma (acoustic neuroma, neurilemmoma, neurinoma, neurolemmoma, Schwann cell tumor), Solitary angiokeratoma, Solitary cutaneous leiomyoma, Solitary mastocytoma, Urticaria pigmentosa, Solitary neurofibroma (plexiform neurofibroma, solitary nerve sheath tumor, sporadic neurofibroma), Spider angioma (nevus araneus, spider telangiectasia, spider nevus, vascular spider), Spindle cell hemangioendothelioma (spindle cell hemangioma), Spindle cell lipoma, Sternal cleft, Subungual exostosis, Superficial acral fibromyxoma, Systemic mastocytosis, Targetoid hemosiderotic hemangioma (hobnail hemangioma), Telangiectasia, Telangiectasia macularis eruptiva perstans, Teratoma, Tufted angioma (acquired tufted angioma, angioblastoma, angioblastoma of Nakagawa, hypertrophic hemangioma, progressive capillary hemangioma, tufted hemangioma), Umbilical granuloma, Universal angiomatosis (generalized telangiectasia), Urticaria pigmentosa (childhood type of generalized eruption of cutaneous mastocytosis), Venous lake (phlebectasis), Wildervanck syndrome, Xanthelasmoidal mastocytosis, Zosteriform metastasis, etc.; Dermatitis such as but not limited to Essential dermatitis, Atopic dermatitis (atopic eczema, disseminated neurodermatitis, flexural eczema, infantile eczema, prurigo diathsique), Contact dermatitis (dermatitis caused by certain substances coming in contact with the skin), Eczema (conditions that begin as spongiotic dermatitis and may progress to a lichenified stage such as but not limited to Autoimmune estrogen dermatitis, Autoimmune progesterone dermatitis, Autosensitization dermatitis, Breast eczema (nipple eczema), Chronic vesiculobullous hand eczema, Circumostomy eczema, Dyshidrosis (acute vesiculobullous hand eczema, cheiropompholyx, dyshidrotic eczema, pompholyx, podopompholyx), Ear eczema, Eyelid dermatitis, Hand eczema, Hyperkeratotic hand dermatitis, Id reaction (disseminated eczema, generalized eczema), Irritant diaper dermatitis (diaper dermatitis, napkin dermatitis), Juvenile plantar dermatosis (atopic winter feet, dermatitis plantaris sicca, forefoot dermatitis, moon-boot foot syndrome, sweaty sock dermatitis), Molluscum dermatitis, Nummular dermatitis (discoid eczema, microbial eczema, nummular eczema, nummular neurodermatitis), Nutritional deficiency eczema, Sulzberger-Garbe syndrome (oid-oid disease), Xerotic eczema (asteatotic eczema, desiccation dermatitis, eczema craquelé, pruritus hiemalis, winter eczema, winter itch), Pustular dermatitis (inflammation of the skin that presents with pustular lesions, such as Eosinophilic pustular folliculitis (Ofuji's disease, sterile eosinophilic pustulosis), Reactive arthritis (Reiter's disease, Reiter's syndrome), Subcorneal pustular dermatosis (Sneddon-Wilkinson disease), Seborrheic dermatitis (chronic, superficial, inflammatory disease characterized by scaling on an erythematous base, such as Infantile seborrheic dermatitis, Leiner's disease, Pityriasis simplex capillitii (dandruff), Seborrheic dermatitis (seborrheic eczema), etc.; Disturbances of human pigmentation (either loss or reduction, may be related to loss of melanocytes or the inability of melanocytes to produce melanin or transport melanosomes correctly) such as but not limited to Albinism-black lock-cell migration disorder of the neurocytes of the gut-deafness syndrome (ABCD syndrome), Albinism-deafness syndrome (Woolf syndrome, Ziprkowski-Margolis syndrome), Alezzandrini syndrome, Argyria Arsenic poisoning, Depigmented patches on the posterior hand and fingers, Vitiligo, Berlin syndrome, Canthaxanthin, Chédiak-Higashi syndrome, Chrysiasis, Cross-McKusick-Breen syndrome (Cross syndrome, oculocerebral-hypopigmentation syndrome), Dermatopathia pigmentosa reticularis (dermatopathia pigmentosa reticularis hyperkeratotica et mutilans, dermatopathia pigmentosa reticularis hypohidotica et atrophica, dermatopathic pigmentosa reticularis), Dyschromatosis symmetrica hereditaria (reticulate acropigmentation of Dohi, symmetrical dyschromatosis of the extremities), Dyschromatosis universalis hereditaria, Elejalde syndrome (Griscelli syndrome type 1), Familial progressive hyperpigmentation, Galli-Galli disease, Griscelli syndrome type 2 (partial albinism with immunodeficiency), Griscelli syndrome type 3, Hemochromatosis (bronze diabetes), Hemosiderin hyperpigmentation, Hermansky-Pudlak syndrome, Idiopathic guttate hypomelanosis (leukopathia symmetrica progressiva), Iron metallic discoloration, Klein-Waardenburg syndrome, Lead poisoning, Leukoderma, Melanoma-associated leukoderma, Melasma (chloasma faciei, mask of pregnancy), Mukamel syndrome, Necklace of Venus, Nevus anemicus, Multiple, hypopigmented macules and patches on the leg of an adult, Nevus anemicus, Nevus depigmentosus (nevus achromicus), Ocular albinism, Oculocutaneous albinism, Pallister-Killian syndrome Periorbital hyperpigmentation, Photoleukomelanodermatitis of Kobori, Phylloid hypomelanosis, Piebaldism, Pigmentatio reticularis faciei et colli, Pityriasis alba, Poikiloderma of Civatte, Poikiloderma vasculare atrophicans, Postinflammatory hyperpigmentation (postinflammatory hypermelanosis), Postinflammatory hypopigmentation, Progressive macular hypomelanosis, Quadrichrome vitiligo, Reticular pigmented anomaly of the flexures (dark dot disease, Dowling-Degos' disease), Reticulate acropigmentation of Kitamura, Revesz syndrome, Riehl melanosis, Scratch dermatitis (flagellate pigmentation from bleomycin), Segmental vitiligo, Shah-Waardenburg syndrome, Shiitake mushroom dermatitis (flagellate mushroom dermatitis, mushroom worker's disease, shiitake-induced toxicoderma), Tar melanosis (melanodermatitis toxica lichenoides), Tietz syndrome, Titanium metallic discoloration, Transient neonatal pustular melanosis (transient neonatal pustulosis, lentigines neonatorum), Trichrome vitiligo, Vagabond's leukomelanoderma, Vasospastic macule, Vitiligo, Vitiligo ponctué, Vogt-Koyanagi-Harada syndrome, Waardenburg syndrome, Wende-Bauckus syndrome (Pegum syndrome), Woronoff's ring, X-linked reticulate pigmentary disorder (familial cutaneous amyloidosis, Partington amyloidosis, Partington cutaneous amyloidosis, Partington syndrome type II, reticulate pigmentary disorder, X-linked reticulate pigmentary disorder with systemic manifestations), Yemenite deaf-blind hypopigmentation syndrome, etc; Drug eruptions are adverse drug reactions that present with cutaneous manifestations; Endocrine conditions, such as but not limited to Acanthosis nigricans associated with malignancy (acanthosis nigricans type I), Acanthosis nigricans associated with obesity, insulin-resistant states, and endocrinopathy (acanthosis nigricans type III), Acral acanthosis nigricans (acral acanthotic anomaly), Acral dry gangrene, Acromegaly, Addison's disease, Adrenal adenoma, Adrenal carcinoma, Adrenal hyperplasia, Alopecia-nail dystrophy-ophthalmic complications-thyroid dysfunction-hypohidrosis-ephelides and enteropathy-respiratory tract infections syndrome (ANOTHER syndrome), Arrhenoblastoma, Cretinism, Cushing's syndrome, Hyperpigmented plaque with velvety textural change within the axillary fold of an adult, Acanthosis nigricans associated with obesity, insulin-resistant states, and endocrinopathy, Excess ovarian androgen release syndrome (ovarian SAHA syndrome), Familial acanthosis nigricans (acanthosis nigricans type II), Growth hormone deficiency, Hyperandrogenism-insulin resistance-acanthosis nigricans syndrome (HAIR-AN syndrome), Hyperparathyroidism, Hyperprolactinemic SAHA syndrome, Hyperthyroidism, Hypoparathyroidism, Hypothyroidism, Leydig cell tumor, Multiple endocrine neoplasia type 1 (Wermer syndrome), Multiple endocrine neoplasia type 2 (multiple endocrine neoplasia type 2A, pheochromocytoma and amyloid-producing medullary thyroid carcinoma, PTC syndrome, Sipple syndrome), Multiple endocrine neoplasia type 3 (mucosal neuromata with endocrine tumors, multiple endocrine neoplasia type 2B, multiple mucosal neuroma syndrome, Wagenmann-Froboese syndrome), Myxedema, Panhypopituitarism, Persistent adrenarche syndrome (adrenal SAHA syndrome), Polycystic ovarian syndrome, Seborrhoea-acne-hirsutism-alopecia (SAHA syndrome), Thyroid acropachy, etc; Eosinophilic cutaneous conditions (diseases that are characterized histologically by the presence of eosinophils in the inflammatory infiltrate, or evidence of eosinophil degranulation) such as but not limited to: Angiolymphoid hyperplasia with eosinophilia (epithelioid hemangioma, histiocytoid hemangioma, inflammatory angiomatous nodule, inflammatory arteriovenous hemangioma, intravenous atypical vascular proliferation, papular angioplasia, pseudopyogenic granuloma), Annular erythema of infancy, Arthropod assault, Eosinophilic cellulitis (Wells' syndrome), Eosinophilic fasciitis (Shulman's syndrome), Eosinophilic granuloma, Eosinophilic granulomatosis with polyangiitis (Churg-Strauss syndrome, allergic granulomatosis), Eosinophilic pustular folliculitis of infancy (eosinophilic pustular folliculitis in infancy, infantile eosinophilic pustular folliculitis, neonatal eosinophilic pustular folliculitis), Eosinophilic ulcer of the oral mucosa (eosinophilic ulcer of the tongue, Riga-Fede disease, traumatic eosinophilic granuloma), Eosinophilic vasculitis, Erythema toxicum neonatorum (erythema toxicum, toxic erythema of the newborn), Granuloma faciale, Hypereosinophilic syndrome, Incontinentia pigmenti (Bloch-Siemens syndrome, Bloch-Sulzberger disease, Bloch-Sulzberger syndrome), Itchy red bump disease (papular dermatitis), Juvenile xanthogranuloma, Kimura's disease, Nodules-eosinophilia-rheumatism-dermatitis-swelling syndrome, Pachydermatous eosinophilic dermatitis, Papular eruption of blacks, Papuloerythroderma of Ofuji, Pruritic papular eruption of HIV disease, etc.; Epidermal nevi, neoplasms, and cysts (skin lesions that develop from the epidermal layer of the skin); Erythemas (reactive skin conditions in which there is blanchable redness) such as but not limited to Erythema annulare centrifugum (deep gyrate erythema, erythema perstans, palpable migrating erythema, superficial gyrate erythema), Erythema gyratum repens (Gammel's disease), Erythema migrans (erythema chronicum migrans), Erythema multiforme, Erythema multiforme minor (herpes simplex-associated erythema multiforme), Erythema palmare, Generalized erythema, Necrolytic acral erythema, Necrolytic migratory erythema (glucagonoma syndrome), etc.; Genodermatoses (inherited genetic skin conditions often grouped into three categories: chromosomal, single gene, and polygenetic) such as but not limited to 18q deletion syndrome, Acrodermatitis enteropathica, Acrogeria (Gottron syndrome), Acrokeratosis verruciformis (acrokeratosis verruciformis of Hopf), Adams-Oliver syndrome, Adducted thumbs syndrome, Albright's hereditary osteodystrophy, Angelman syndrome, Apert syndrome (acrocephalosyndactyly), Arthrogryposis-renal dysfunction-cholestasis syndrome, Ataxia telangiectasia (Louis-Bar syndrome), Atrichia with papular lesions (papular atrichia), Atrophodermia vermiculata (acne vermoulante, acne vermoulanti, atrophoderma reticulata symmetrica faciei, atrophoderma reticulatum, atrophoderma vermiculata, atrophoderma vermiculatum, atrophodermia reticulata symmetrica faciei, atrophodermia ulerythematosa, atrophodermie vermiculée des joues avec keratoses folliculaires, folliculitis ulerythema reticulata, folliculitis ulerythematous reticulata, folliculitis ulerythemosa, honeycomb atrophy, ulerythema acneforme, ulerythema acneiforme), Autoimmune polyendocrinopathy-candidiasis-ectodermal dystrophy syndrome, Bart syndrome, Bazex-Dupré-Christol syndrome (Bazex syndrome, follicular atrophoderma and basal cell cacinomas), Beare-Stevenson cutis gyrata syndrome, Bloom syndrome (Bloom-Torre-Machacek syndrome), Blue rubber bleb nevus syndrome, Brittle hair-intellectual impairment-decreased fertility-short stature syndrome, Cantu syndrome, Cardio-facio-cutaneous syndrome (cardiofaciocutaneous syndrome), Cartilage-hair hypoplasia (McKusick type metaphyseal chondrodysplasia), Cerebral dysgenesis-neuropathy-ichthyosis-keratoderma syndrome, Childhood tumor syndrome, Chondrodysplasia punctata, Cicatricial junctional epidermolysis bullosa, Craniosynostosis-anal anomalies-porokeratosis syndrome, Cockayne syndrome, Colobomas of the eye-heart defects-ichthyosiform dermatosis-mental retardation-ear defects syndrome (CHIME syndrome, Zunich neuroectodermal syndrome, Zunich-Kaye syndrome), Congenital hemidysplasia with ichthyosiform erythroderma and limb defects syndrome (CHILD syndrome), Conradi-Hünermann syndrome (Conradi-Hünermann-Happle syndrome, Happle syndrome, X-linked dominant chondrodysplasia punctata), Costello syndrome, Cronkhite-Canada syndrome, Crouzon syndrome, Cutis verticis gyrata, Darier's disease (Darier-White disease, dyskeratosis follicularis, keratosis follicularis), Linear Darier disease, DeSanctis-Cacchione syndrome, Disseminated superficial actinic porokeratosis, Disseminated superficial porokeratosis, Dolichol kinase deficiency, Dominant dystrophic epidermolysis bullosa, Dyskeratosis congenita (Zinsser-Cole-Engman syndrome), Dystrophic epidermolysis bullosa, Ectodermal dysplasia, Ectodermal dysplasia with corkscrew hairs, Ectrodactyly-ectodermal dysplasia-cleft syndrome (EEC syndrome, split hand-split foot-ectodermal dysplasia-cleft syndrome), Epidermolysis bullosa herpetiformis (Dowling-Meara epidermolysis bullosa simplex), Epidermolysis bullosa simplex, Epidermolysis bullosa simplex of Ogna, Epidermolysis bullosa simplex with mottled pigmentation, Epidermolysis bullosa simplex with muscular dystrophy, Epidermolytic hyperkeratosis (bullous congenital ichthyosiform erythroderma, bullous ichthyosiform erythroderma), Erythrokeratodermia with ataxia (Giroux-Barbeau syndrome), Familial benign chronic pemphigus (familial benign pemphigus, Hailey-Hailey disease), Fanconi syndrome (familial pancytopenia, familial panmyelophthisis), Fibrodysplasia ossificans progressiva, Focal dermal hypoplasia (Goltz syndrome), Follicular atrophoderma, Franceschetti-Klein syndrome (mandibulofacial dysostosis), Gardner's syndrome (familial colorectal polyposis), Gastrocutaneous syndrome, Generalized atrophic benign epidermolysis bullosa, Generalized epidermolysis bullosa simplex (Koebner variant of generalized epidermolysis bullosa simplex), Generalized trichoepithelioma, Giant axonal neuropathy with curly hair, Gingival fibromatosis with hypertrichosis, Haber syndrome, Hallerman-Streiff syndrome, Harlequin-type ichthyosis (harlequin baby, harlequin fetus, harlequin ichthyosis, ichthyosis congenita, ichthyosis congenita gravior), Hay-Wells syndrome (AEC syndrome, ankyloblepharon filiforme adnatum-ectodermal dysplasia-cleft palate syndrome, ankyloblepharon-ectodermal defects-cleft lip and palate syndrome, ankyloblepharon-ectodermal dysplasia-clefting syndrome), Hereditary sclerosing poikiloderm, Keratosis pilaris, Heterochromia iridum, Holocarboxylase synthetase deficiency, Hypohidrotic ectodermal dysplasia (anhidrotic ectodermal dysplasia, Christ-Siemens-Touraine syndrome), Hypotrichosis-acro-osteolysis-onychogryphosis-palmoplantar keratoderma-periodontitis syndrome, Hypotrichosis-lymphedema-telangiectasia syndrome, Ichthyosis-brittle hair-impaired intelligence-decreased fertility-short stature syndrome (IBIDS syndrome, sulfur-deficient brittle hair syndrome, Tay's syndrome, trichothiodystrophy, trichothiodystrophy with ichthyosis), Ichthyosis bullosa of Siemens (ichthyosis exfoliativa), Ichthyosis follicularis (ichthyosis follicularis with alopecia and photophobia syndrome), Ichthyosis linearis circumflexa, Ichthyosis prematurity syndrome, Ichthyosis vulgaris (autosomal dominant ichthyosis, ichthyosis simplex), Ichthyosis with confetti, Neonatal ichthyosis-sclerosing cholangitis syndrome (ichthyosis-sclerosing cholangitis syndrome, NISCH syndrome), Incontinentia pigmenti achromians (hypomelanosis of Ito), Immune dysfunction-polyendocrinopathy-enteropathy-X-linked syndrome, Jaffe-Campanacci syndrome, Johanson-Blizzard syndrome, Johnson-McMillin syndrome, Joubert syndrome, Junctional epidermolysis bullosa, Junctional epidermolysis bullosa gravis (epidermolysis bullosa letalis, Herlitz disease, Herlitz epidermolysis bullosa, Herlitz syndrome, lethal junctional epidermolysis bullosa), Junctional epidermolysis bullosa with pyloric atresia, Kabuki syndrome (Kabuki makeup syndrome, Niikawa-Kuroki syndrome), Keratolytic winter erythema (erythrokeratolysis hiemalis, Oudtshoorn disease, Oudtshoorn skin), Keratosis follicularis spinulosa decalvans (Siemens-1 syndrome), Keratosis linearis with ichthyosis congenital and sclerosing keratoderma syndrome, Keratosis pilaris atrophicans faciei (folliculitis rubra, keratosis pilaris rubra atrophicans faciei, lichen pilare, lichen pilaire ou xerodermie pilaire symmetrique de la face', ulerythema ophryogenes, xerodermi pilaire symmetrique de la face), Keratosis pilaris, Kindler syndrome (acrokeratotic poikiloderma, bullous acrokeratotic poikiloderma of Kindler and Weary, congenital poikiloderma with blisters and keratoses, congenital poikiloderma with bullae and progressive cutaneous atrophy, hereditary acrokeratotic poikiloderma, hyperkeratosis-hyperpigmentation syndrome, Weary-Kindler syndrome), Klinefelter syndrome, Klippel-Feil syndrome, Lamellar ichthyosis (collodion baby), Legius syndrome (neurofibromatosis type 1-like syndrome), Lelis syndrome, Lenz-Majewski syndrome, Leschke syndrome, Lethal acantholytic epidermolysis bullosa, Lhermitte-Duclos disease, Linear and whorled nevoid hypermelanosis (linear nevoid hyperpigmentation, progressive cribriform and zosteriform hyperpigmentation, reticulate and zosteriform hyperpigmentation, reticulate hyperpigmentation of Iijima and Naito and Uyeno, zebra-like hyperpigmentation in whorls and streaks, zebra-line hyperpigmentation), Linear Darier disease (acantholytic dyskeratotic epidermal nevus), Linear porokeratosis, Localized epidermolysis bullosa simplex (Weber-Cockayne syndrome, Weber-Cockayne variant of generalized epidermolysis bullosa simplex), Mandibuloacral dysplasia, Marinesco-Sjögren syndrome, McCune-Albright syndrome, McCusick syndrome, Metageria, Microphthalmia-dermal aplasia-sclerocornea syndrome, Mitis junctional epidermolysis bullosa (nonlethal junctional epidermolysis bullosa), Mitochondrial myopathy-encephalopathy-lactic acidosis-stroke syndrome, Multiple lentigines syndrome (cardiocutaneous syndrome, Gorlin syndrome II, lentiginosis profusa syndrome-LEOPARD syndrome, progressive cardiomyopathic lentiginosis), Multiple pterygium syndrome, Multiple sulfatase deficiency (Austin disease, mucosulfatidosis), Naegeli-Franceschetti-Jadassohn syndrome (chromatophore nevus of Naegeli), Netherton syndrome, Neurofibromatosis type 1 (von Recklinghausen's disease), Neurofibromatosis type 1, Neurofibromatosis type 3 (neurofibromatosis mixed type), Neurofibromatosis type 4 (neurofibromatosis variant type), Neutral lipid storage disease (Dorfman-Chanarin syndrome), Nonbullous congenital ichthyosiform erythroderma (congenital ichthyosiform erythroderma), Noonan syndrome, Oculocerebrocutaneous syndrome (Delleman-Oorthuys syndrome), Oculodentodigital dysplasia, Odonto-Tricho-Ungual-Digital, Palmar syndrome, Oliver-McFarlane syndrome, Orofaciodigital syndrome, Pachydermoperiostosis (idiopathic hypertrophic osteoathorpathy, Touraine-Solente-Gole syndrome), Peeling skin syndrome (acral peeling skin syndrome, continual peeling skin syndrome, familial continual skin peeling, idiopathic deciduous skin, keratolysis exfoliativa congenita), Pfeiffer syndrome, Photosensitivity-ichthyosis-brittle sulfur-deficient hair-impaired intelligence-decreased fertility-short stature syndrome, Pityriasis rotunda (pityriasis circinata, tinea circinata), Plate-like osteoma cutis, Plaque-type porokeratosis (classic porokeratosis, porokeratosis of Mibelli), Polyneuropathy-organomegaly-endocrinopathy-monoclonal gammopathy-skin changes syndrome (Crow-Fukase syndrome), Polyostotic fibrous dysplasia (Albright's disease), Popliteal pterygium syndrome, Porokeratosis, Porokeratosis palmaris et plantaris disseminata, Prader-Willi syndrome, Progeria (Hutchinson-Gilford progeria syndrome, Hutchinson-Gilford syndrome, progeria syndrome), Progressive osseous heteroplasia, Progressive symmetric erythrokeratodermia (erythrokeratodermia progressiva symmetrica), Proteus syndrome, Proteus-like syndrome, Punctate porokeratosis, Rapp-Hodgkin syndrome (Rapp-Hodgkin ectodermal dysplasia syndrome), Recessive dystrophic epidermolysis bullosa (Hallopeau-Siemens variant of epidermolysis bullosa, Hallopeau-Siemens disease), Refsum's disease (heredopathia atactica polyneuritiformis, phytanic acid storage disease), Relapsing linear acantholytic dermatosis, Restrictive dermopathy, X-linked ichthyosis, Rhizomelic chondrodysplasia punctata (autosomal recessive chondrodysplasia punctata type 1, chondrodystrophia calcificans punctata, peroxisomal biogenesis disorder complementation group 11), Rombo syndrome, Rothmund-Thomson syndrome (poikiloderma congenitale), Rud syndrome, Say syndrome, Scalp-ear-nipple syndrome (Finlay-Marks syndrome), Schindler disease (Kanzaki disease, alpha-N-acetylgalactosaminidase deficiency), Schinzel-Giedion syndrome, Scleroatrophic syndrome of Huriez (Huriez syndrome, palmoplantar keratoderma with scleroatrophy, palmoplantar keratoderma with sclerodactyly, scleroatrophic and keratotic dermatosis of the limbs, sclerotylosis), Segmental neurofibromatosis, Senter syndrome (Desmons' syndrome), Shabbir syndrome (laryngo-onycho-cutaneous syndrome), Silver-Russell syndrome, Sjögren-Larsson syndrome, Skin fragility syndrome (plakophilin 1 deficiency), Smith-Lemli-Opitz syndrome, Sturge-Weber syndrome, Supernumerary nipples-uropathies-Becker's nevus syndrome, Terminal osseous dysplasia with pigmentary defects, Tooth and nail syndrome (hypodontia with nail dysgenesis, Witkop syndrome), Townes-Brocks syndrome, Transient bullous dermolysis of the newborn, Treacher Collins syndrome (Treacher Collins-Franceschetti syndrome), Tricho-dento-osseous syndrome, Tricho-rhino-phalangeal syndrome, Tuberous sclerosis (Bourneville disease, epiloia), Turner syndrome, Ulnar-mammary syndrome, Van Der Woude syndrome, Von Hippel-Lindau syndrome, Watson syndrome, Werner syndrome (adult progeria), Westerhof syndrome, Whistling syndrome (craniocarpotarsal syndrome, distal arthrogryposis type 2, Freeman-Sheldon syndrome, Windmill-Vane-Hand syndrome), Wilson-Turner syndrome, Wolf-Hirschhorn syndrome (4p-syndrome), X-linked ichthyosis (steroid sulfatase deficiency, X-linked recessive ichthyosis), X-linked recessive chondrodysplasia punctata, Xeroderma pigmentosum (Cockayne syndrome complex), XXYY genotype, Zimmermann-Laband syndrome, etc.; Infection-related cutaneous conditions may be caused by bacteria, fungi, yeast, viruses, and/or parasites; Lichenoid eruptions (dermatoses related to the unique, common inflammatory disorder lichen planus, which affects the skin, mucous membranes, nails, and hair) such as but not limited to Annular lichen planus, Violaceous, Lichen planus actinicus, Atrophic lichen planus, Bullous lichen planus (vesiculobullous lichen planus), Erosive lichen planus, Erythema dyschromicum perstans (ashy dermatosis, dermatosis cinecienta), Giant cell lichenoid dermatitis, Hepatitis-associated lichen planus, Hypertrophic lichen planus (lichen planus verrucosus), Idiopathic eruptive macular pigmentation, Inverse lichen planus, Keratosis lichenoides chronica (Nékam's disease), Kraurosis vulvae, Lichen nitidus, Lichen planus actinicus (actinic lichen niditus, actinic lichen planus, lichen planus atrophicus annularis, lichen planus subtropicus, lichen planus tropicus, lichenoid melanodermatitis, lichenoid melanodermatosis, summertime actinic lichenoid eruption), Lichen planus pemphigoides, Lichen planus pigmentosus, Lichen nitidus, Lichen planus-lichen sclerosus overlap syndrome, Lichen ruber moniliformis, Lichen sclerosus (lichen sclerosus et atrophicus), Lichen striatus (Blaschko linear acquired inflammatory skin eruption, linear lichenoid dermatosis), Lichen verrucosus et reticularis, Lichenoid trikeratosis, Lichenoid dermatitis, Lichenoid reaction of graft-versus-host disease, Linear lichen planus, Mucosal lichen planus, Peno-gingival syndrome, Ulcerative lichen planus, Vulvovaginal gingival syndrome, Vulvovaginal lichen planus, etc.; Lymphoid-related cutaneous conditions disorders characterized by collections of lymphocyte cells within the skin) such as but not limited to Adult T-cell leukemia/lymphoma, Angiocentric lymphoma (extranodal natural killer cell lymphoma, nasal-type NK lymphoma, NK/T-cell lymphoma, polymorphic/malignant midline reticulosis), Angioimmunoblastic T-cell lymphoma (angioimmunoblastic lymphadenopathy with dysproteinemia), Blastic NK-cell lymphoma, CD30+ cutaneous T-cell lymphoma (primary cutaneous anaplastic large cell lymphoma), Cutaneous lymphoid hyperplasia (borrelial lymphocytoma, lymphadenosis benigna cutis, lymphocytoma cutis, pseudolymphoma, pseudolymphoma of Spiegler and Fendt, sarcoidosis of Spiegler and Fendt, Spiegler-Fendt lymphoid hyperplasia, Spiegler-Fendt sarcoid), A solitary, large, red papule on the left cheek of an adult male, Cutaneous lymphoid hyperplasia, Cutaneous lymphoid hyperplasia with bandlike and perivascular patterns, Cutaneous lymphoid hyperplasia with nodular pattern (nodular pattern of cutaneous lymphoid hyperplasia), Diffuse large B-cell lymphoma (primary cutaneous large B-cell lymphoma), Granulocytic sarcoma (chloroma, myeloid sarcoma), Granulomatous slack skin, Hairy-cell leukemia, Hodgkin's disease, Ichthyosis acquisita (acquired ichthyosis), IgG4-related skin disease, Intravascular large B-cell lymphoma (angiotropic large cell lymphoma, intralymphatic lymphomatosis, intravascular lymphomatosis, malignant angioendotheliomatosis), Jessner lymphocytic infiltrate of the skin (benign lymphocytic infiltration of the skin, Jessner lymphocytic infiltration of the skin, Jessner-Kanof lymphocytic infiltration of the skin, lymphocytic infiltrate of Jessner), Kikuchi's disease (histiocytic necrotizing lymphadenitis), Large plaque parapsoriasis (parapsoriasis en plaques), Lennert lymphoma (lymphoepitheliod lymphoma), Leukemia cutis, Lymphoma cutis, Lymphomatoid granulomatosis, Lymphomatoid papulosis, Malignant histiocytosis (histiocytic medullary reticulosis), Marginal zone B-cell lymphoma, Mucosa-associated lymphoid tissue lymphoma, Mycosis fungoides, Non-mycosis fungoides CD30-cutaneous large T-cell lymphoma, Nonspecific cutaneous conditions associated with leukemia (leukemid), Pagetoid reticulosis (acral mycoses fungoides, localized epidermotropic reticulosis, mycosis fungoides palmaris et plantaris, unilesional mycosis fungoides, Woringer-Kolopp disease), Pityriasis lichenoides chronica (chronic guttate parapsoriasis, chronic pityriasis lichenoides, dermatitis psoriasiformis nodularis, parapsoriasis chronica, parapsoriasis lichenoides chronica), Pityriasis lichenoides et varioliformis acuta (acute guttate parapsoriasis, acute parapsoriasis, acute pityriasis lichenoides, Mucha-Habermann disease, parapsoriasis acuta, parapsoriasis lichenoides et varioliformis acuta, parapsoriasis varioliformis), Plasmacytoma, Plasmacytosis, Pleomorphic T-cell lymphoma (non-mycosis fungoides CD30-pleomorphic small/medium-sized cutaneous T-cell lymphoma), Polycythemia vera (erythremia), Primary cutaneous follicular lymphoma (follicular center cell lymphoma, follicular center lymphoma), Primary cutaneous immunocytoma, Primary cutaneous marginal zone lymphoma, Retiform parapsoriasis, Secondary cutaneous CD30+ large cell lymphoma, Sezary syndrome, Sinus histiocytosis with massive lymphadenopathy (Rosai-Dorf man disease), Subcutaneous T-cell lymphoma (panniculitis-like T-cell lymphoma), Vesiculopustular eruption and leukemoid reaction in Down syndrome, etc.; Melanocytic nevi and neoplasms such as but not limited to Acral nevus (melanocytic nevus of acral skin, melanocytic nevus with intraepidermal ascent of cells), Amelanotic blue nevus (hypomelanotic blue nevus), Becker's nevus, Balloon cell nevus, Bannayan-Riley-Ruvalcaba syndrome Becker's nevus (Becker's melanosis, Becker's pigmentary hamartoma, nevoid melanosis, pigmented hairy epidermal nevus), Benign melanocytic nevus (banal nevus, common acquired melanocytic nevus, mole, nevocellular nevus, nevocytic nevus), Blue nevus (blue neuronevus, dermal melanocytoma, nevus bleu), Blue nevus of Jadassohn-Ti-che (common blue nevus, nevus ceruleus), Carney complex (LAMB syndrome, NAME syndrome), Cellular blue nevus, Centrofacial lentiginosis, Congenital melanocytic nevus, Deep penetrating nevus, Dysplastic nevus (atypical mole, atypical nevus, B-K mole, Clark's nevus, dysplastic melanocytic nevus, nevus with architectural disorder), Dysplastic nevus syndrome (B-K mole syndrome, familial atypical multiple mole-melanoma syndrome, familial melanoma syndrome), Ephelis (freckle), Epithelioid blue nevus, Generalized lentiginosis, Giant pigmented nevus (bathing trunk nevus, congenital nevomelanocytic nevus, garment nevus, giant hairy nevus, nevus pigmentosus et pilosus), Halo nevus (leukoderma acquisitum centrifugum, perinevoid vitiligo, Sutton nevus), Hori's nevus (acquired bilateral nevus of Ota-like macules), Inherited patterned, lentiginosis in black persons, Ink spot lentigo (sunburn lentigo), Laugier-Hunziker syndrome, Lentigo simplex (simple lentigo), Malignant blue nevus, Medium-sized congenital nevocytic nevus, Melanoacanthoma, Melanocytic tumors of uncertain malignant potential, Moynahan syndrome, Mucosal lentigines (labial and penile and vulvar melanosis, melanotic macules), Nevus of Ito (nevus fuscoceruleus acromiodeltoideus), Nevus of Ota (congenital melanosis bulbi, melanosis bulborum and aberrant dermal melanocytosis, nevus fuscoceruleus ophthalmomaxillaris, oculodermal melanocytosis, oculomucodermal melanocytosis), Nevus spilus (speckled lentiginous nevus, zosteriform lentiginous nevus), Partial unilateral lentiginosis (segmental lentiginosis), Peutz-Jeghers syndrome, Pigmented spindle cell nevus (pigmented spindle cell tumor of Reed, pigmented variant of Spitz nevus), Pseudomelanoma (recurrent melanocytic nevus, recurrent nevus), PUVA lentigines, Small-sized congenital nevocytic nevus, Spitz nevus (benign juvenile melanoma, epithelioid and spindle cell nevus, Spitz's juvenile melanoma), Solar lentigo (lentigo senilis, liver spot, old age spot, senile freckle), etc.; Melanoma (malignant proliferation of melanocytes and the most aggressive type of skin cancer) such as Acral lentiginous melanoma, Amelanotic melanoma, Animal-type melanoma, Desmoplastic melanoma (neurotropic melanoma, spindled melanoma), Lentigo maligna (lentiginous melanoma on sun-damaged skin), Lentigo maligna melanoma, Melanoma with features of a Spitz nevus (Spitzoid melanoma), Melanoma with small nevus-like cells (small cell melanoma), Mucosal melanoma, Nevoid melanoma, Nodular melanoma, Polypoid melanoma, Seborrheic keratosis-like melanoma Soft-tissue melanoma (clear-cell sarcoma, melanoma of the soft parts), Superficial spreading melanoma (superficially spreading melanoma), Uveal melanoma, etc.; Monocyte- and macrophage-related cutaneous conditions (conditions that are characterized histologically by infiltration of the skin by monocyte and/or macrophage cells, often divided into several categories, including granulomatous disease, histiocytoses, and sarcoidosis); Mucinoses (conditions caused by dermal fibroblasts producing abnormally large amounts of mucopolysaccharides); Neurocutaneous (conditions due to organic nervous system disease or are psychiatric in etiology) such as but not limited to Atypical chronic pain syndrome, Body dysmorphic disorder (dysmorphic syndrome, dysmorphophobia), Brachioradial pruritus, Bromidrosiphobia, Complex regional pain syndrome (reflex sympathetic dystrophy), Congenital insensitivity to pain with anhidrosis, Delusional parasitosis (delusions of parasitosis, Ekbom syndrome, monosymptomatic hypochondriacal psychosis), Dermatothlasia, Factitious dermatitis (dermatitis artefacta, factitial dermatitis), Factitious dermatitis, Glossodynia (burning mouth syndrome, burning tongue, orodynia), Levator ani syndrome, Malum perforans pedis (neurotrophic ulcer, perforating ulcer of the foot), Meralgia paresthetica (Roth-Bernhardt disease), Neurotic excoriations, Notalgia paresthetica (hereditary localized pruritus, posterior pigmented pruritic patch, subscapular pruritus), Postencephalitic trophic ulcer, Psychogenic pruritus, Riley-Day syndrome (familial dysautonomia), Scalp dysesthesia, Sciatic nerve injury, Scrotodynia, Syringomyelia (Morvan's disease), Traumatic neuroma (amputation neuroma), Trichotillomania (trichotillosis), Trigeminal neuralgia (tic douloureux), Trigeminal trophic lesion (trigeminal trophic syndrome), Vulvodynia (vestibulodynia), etc.; Noninfectious immunodeficiency-related cutaneous conditions (conditions caused by T-cell and/or B-cell dysfunction) such as but not limited to Bare lymphocyte syndrome, Chronic granulomatous disease (Bridges-Good syndrome, chronic granulomatous disorder, Quie syndrome), Common variable immunodeficiency (acquired hypogammaglobulinemia), Complement deficiency, DiGeorge syndrome (DiGeorge anomaly, thymic hypoplasia), Graft-versus-host disease, Griscelli syndrome, Hyper-IgE syndrome (Buckley syndrome, Job syndrome), Immunodeficiency with hyper-IgM, Immunodeficiency-centromeric instability-facial anomalies syndrome (ICF syndrome), Isolated IgA deficiency, Isolated primary IgM deficiency, Janus kinase 3 deficiency, Leukocyte adhesion molecule deficiency, LIG4 syndrome, Myeloperoxidase deficiency, Neutrophil immunodeficiency syndrome, Nezelof syndrome (thymic dysplasia with normal immunoglobulins), Omenn syndrome, Purine nucleoside phosphorylase deficiency, Severe combined immunodeficiency (alymphocytosis, Glanzmann-Riniker syndrome, severe mixed immunodeficiency syndrome, thymic alymphoplasia), Shwachman-Bodian-Diamond syndrome, Thymoma with immunodeficiency (Good syndrome), Transient hypogammaglobulinemia of infancy, Warts-hypogammaglobulinemia-infections-myelokathexis syndrome (WHIM syndrome), Wiskott-Aldrich syndrome, X-linked agammaglobulinemia (Bruton syndrome, sex-linked agammaglobulinemia), X-linked hyper-IgM syndrome, X-linked hypogammaglobulinemia, X-linked lymphoproliferative disease (Duncan's disease), X-linked neutropenia, etc.; Papulosquamous hyperkeratotic cutaneous conditions (conditions that present with papules and scales caused by a thickening of the stratum corneum) such as but not limited to Pityriasis rosea, Confluent and reticulated papillomatosis (confluent and reticulated papillomatosis of Gougerot and Carteaud, familial cutaneous papillomatosis, familial occurrence of confluent and reticulated papillomatosis), Digitate dermatosis, Drug-induced keratoderma, Exfoliative dermatitis (dermatitis exfoliativa, erythroderma, red man syndrome), Florid cutaneous papillomatosis, Granular parakeratosis (axillary granular parakeratosis, intertriginous granular parakeratosis), Keratolysis exfoliativa (lamellar dyshidrosis, recurrent focal palmar peeling, recurrent palmar peeling), Keratosis punctata of the palmar creases (hyperkeratosis penetrans, hyperkeratosis punctata, keratodermia punctata, keratosis punctata, keratotic pits of the palmar creases, lenticular atrophia of the palmar creases, punctate keratosis of the palmar creases), Meesmann corneal dystrophy, Paraneoplastic keratoderma, Pityriasis rosea (pityriasis rosea Gibert), Pityriasis rubra pilaris (Devergie's disease, lichen ruber acuminatus, lichen ruber pilaris), Pure hair-nail type ectodermal dysplasia, Small plaque parapsoriasis (chronic superficial dermatitis), Tripe palms, Xanthoerythrodermia perstans, etc.; Palmoplantar keratodermas (hereditary and acquired keratodermas in which there is hyperkeratosis of the skin of the palms and soles); Pruritus, (itchiness) such as but not limited to Adult blaschkitis, Aquadynia, Aquagenic pruritus, Biliary pruritus, Cholestatic pruritus, Drug-induced pruritus, Hydroxyethyl starch-induced pruritus, Lichen simplex chronicus (neurodermatitis), Lichen simplex chronicus, Prion pruritus, Prurigo nodularis, Prurigo pigmentosa, Prurigo simplex, Pruritus ani, Pruritus scroti, Pruritus vulvae, Puncta pruritica (itchy points), Scalp pruritus, Senile pruritus, Uremic pruritus (renal pruritus), etc.; Psoriasis (inflammatory disease of the skin characterized by circumscribed, erythematous, dry, scaling plaques) such as but not limited to Psoriasis vulgaris, Annular pustular psoriasis, Drug-induced psoriasis, Exanthematic pustular psoriasis, Generalized pustular psoriasis (pustular psoriasis of von Zumbusch), Guttate psoriasis (eruptive psoriasis), Inverse psoriasis, Keratoderma blennorrhagica (keratoderma blennorrhagicum), Localized pustular psoriasis, Napkin psoriasis, Psoriasis vulgaris (chronic stationary psoriasis, plaque-like psoriasis), Psoriatic arthritis, Psoriatic erythroderma (erythrodermic psoriasis), Seborrheic-like psoriasis (sebopsoriasis, seborrhiasis), etc.; Reactive neutrophilic cutaneous conditions (diseases mediated by neutrophils, and typically associated with underlying diseases, such as inflammatory bowel disease and hematologic malignancy) including but not limited to Acute erythema nodosum, Bowel-associated dermatosis-arthritis syndrome (bowel bypass syndrome, bowel bypass syndrome without bowel bypass, intestinal bypass arthritis-dermatitis syndrome), Marshall syndrome, Neutrophilic dermatosis of the dorsal hands (pustular vasculitis of the dorsal hands), Neutrophilic eccrine hidradenitis, Pyoderma gangrenosum, Pyogenic arthritis-pyoderma gangrenosum-acne syndrome (PAPA syndrome), Rheumatoid neutrophilic dermatitis (rheumatoid neutrophilic dermatosis), Superficial granulomatous pyoderma, Sweet's syndrome (acute febrile neutrophilic dermatosis), Sweet's syndrome-like dermatosis, Vesicopustular dermatosis, etc.; Recalcitrant palmoplantar eruptions (skin conditions of the palms and soles which are resistant to treatment) such as but not limited to Dermatitis repens (acrodermatitis continua, acrodermatitis continua of Hallopeau, acrodermatitis continua suppurativa Hallopeau, acrodermatitis perstans, dermatitis repens Crocker, Hallopeau's acrodermatitis, Hallopeau's acrodermatitis continua, pustular acrodermatitis), Infantile acropustulosis (acropustulosis of infancy), Palmoplantar pustulosis (persistent palmoplantar pustulosis, pustular psoriasis of the Barber type, pustular psoriasis of the extremities, pustulosis of palms and soles, pustulosis palmaris et plantaris), Pustular bacterid; Skin conditions resulting from errors in metabolism are caused by enzymatic defects that lead to an accumulation or deficiency of various cellular components, including, but not limited to, amino acids, carbohydrates, and lipids; Urticaria (a vascular reaction of the skin characterized by the appearance of wheals, which are firm, elevated swelling of the skin) such as but not limited to Acquired C1 esterase inhibitor deficiency, Acute urticaria, Adrenergic urticaria, Anaphylaxis, Aquagenic urticaria, Cholinergic urticaria, Chronic urticaria (ordinary urticaria), Cold urticaria, Dermatographism (dermographism), Episodic angioedema with eosinophilia (Gleich's syndrome), Exercise urticaria (exercise-induced urticaria), Galvanic urticaria, Heat urticaria, Hereditary angioedema (Quincke's edema), Localized heat contact urticaria, Mast cell-independent urticaria, Physical urticaria, Primary cold contact urticaria, Pressure urticaria (delayed pressure urticaria), Reflex cold urticaria, Schnitzler syndrome, Secondary cold contact urticaria, Solar urticaria, Systemic capillary leak syndrome, Urticarial allergic eruption, Urticaria-like follicular mucinosis, Vibratory angioedema, etc.; and Vascular-related cutaneous conditions result from dysfunction of the blood and/or blood vessels in the dermis, or lymphatics in the subcutaneous tissues.

In some instances, the dermatological condition is Diseases of the skin and subcutaneous tissue, as listed in Chapter XII of The International Statistical Classification of Diseases and Related Health Problems 10th Revision (ICD-10) by the World Health Organization (WHO).

In some instances, the dermatological condition is a condition classified as: Dermatoses Resulting from Physical Factors; Pruritus and Neurocutaneous Dermatoses; Atopic Dermatitis, Eczema, and Noninfectious Immunodeficiency Disorders; Contact Dermatitis and Drug Eruptions; Erythema and Urticaria; Connective Tissue Diseases; Mucinoses; Seborrheic Dermatitis, Psoriasis, Recalcitrant Palmoplantar Eruptions, Pustular Dermatitis, and Erythroderma; Pityriasis Rosea, Pityriasis Rubra Pilaris, and Other Papulosquamous and Hyperkeratotic Diseases; Lichen Planus and Related Conditions; Acne; Bacterial Infections; Diseases Resulting from Fungi and Yeasts; Mycobacterial Diseases; Hansen's Disease; Syphilis, Yaws, Bejel, and Pinta; Viral Diseases; Parasitic Infestations, Stings, and Bites; Chronic Blistering Dermatoses; Nutritional Diseases; Diseases of Subcutaneous Fat; Endocrine Diseases; Abnormalities of Dermal Fibrous and Elastic Tissue; Errors in Metabolism; Genodermatoses and Congenital Anomalies; Dermal and Subcutaneous Tumors; Epidermal Nevi, Neoplasms, and Cysts; Melanocytic Nevi and Neoplasms; Macrophage/Monocyte Disorders; Cutaneous Lymphoid Hyperplasia, Cutaneous T-Cell Lymphoma, Other Malignant Lymphomas, and Allied Diseases; Diseases of the Skin Appendages; Disorders of the Mucous Membranes; Cutaneous Vascular Diseases; or Disturbances of Pigmentation.

In some instances, the dermtalogical condition is selected from the following set of dermatological conditions: dermatitis, e.g., atopic dermatitis, allergic contact dermatitis, irritant contact dermatitis, radiation dermatitis, seborrheic dermatitis; psoriasis; sunburn; ulcers, e.g., diabetic ulcers, pressure ulcers, and stasis ulcers; acne; rosacea; rhytides (wrinkles); hyperhidrosis (excessive sweating); hyperpigmentation; etc.

In some instances, the methods are method of treating dermatitis. Dermatitis is conventionally known as inflammation of the skin and is characterized by itchiness, red skin and rashes, Specific types of dermatitis that may be treated by methods of the invention include: atopic dermatitis, allergic contact dermatitis, irritant contact dermatitis, radiation dermatitis, seborrheic dermatitis, and the like. In some instances where the target dermatological condition is dermatitis, the neuromodulatory agent is not olopatadine hydrochloride (2-[(11Z)-11-[3-(dimethylamino)propylidene]-6H-benzo[c][1]benzoxepin-2-yl]acetic acid; hydrochloride), VUF-K-8788 (7-[3-[4-(2-quinolinylmethyl)-1-piperazinyl]-propoxy]-2,3-dihydro-4H-1,4-benzothiazin-3-one), or bicarphen (1-azoniabicyclo[2.2.2]octan-3-yl-bis(2-methylphenyl)methanol; chloride). In some instances where the target dermatological condition is dermatitis, the neuromodulatory agent is not a non-steroidal anti-inflammatory agent, histamine H1 receptor antagonist, histamine receptor antagonist, or anti-allergic agent. In some instances where the target dermatological condition is dermatitis, the neuromodulatory agent is not naloxone ((4R,4aS,7aR,12bS)-4a,9-dihydroxy-3-prop-2-enyl-2,4,5,6,7a,13-hexahydro-1H-4,12-methanobenzofuro[3,2-e]isoquinoline-7-one), naltrexone ((4R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one), or a gastrin-releasing peptide receptor antagonist. In some instances where the target dermatological condition is dermatitis, the neuromodulatory agent is not a κ-opioid receptor antagonist, δ-opioid receptor antagonist, μ-opioid receptor antagonist, and opioid receptor antagonist, or analgesic. In some instances where the target dermatological condition is dermatitis, the neuromodulatory agent is not tacrolimus, matrine, botulinum toxin (Botox) type A, or pimecrolimus. In some embodiments, the agent is not a macrolide, quinolizidine alkaloid, phenylpropanoid, polyketide, alkaloid, calcineurin inhibitor, κ-opioid receptor antagonist, μ-opioid receptor antagonist, skeletal muscle relaxant, neuromuscular blocking agent, non-steroidal anti-inflammatory compound, disease modifying anti-rheumatic drug, neurotoxic protein, neuromuscular blocking agent, or immunosuppressant. In some instances where the target dermatological condition is dermatitis, the neuromodulatory agent is not SB242084 (6-chloro-5-methyl-N-[6-(2-methylpyridin-3-yl)oxypyridin-3-yl]-2,3-dihydroindole-1-carboxamide), ondansetron (9-methyl-3-[(2-methylimidazol-1-yl)methyl]-2,3-dihydro-1H-carbazol-4-one), capsaicin, or bicarphen (1-azoniabicyclo[2.2.2]octan-3-yl-bis(2-methylphenyl)methanol; chloride). In some instances where the target dermatological condition is dermatitis, the agent is not a 5-HT$_{2c}$ receptor antagonist, 5-HT$_3$ receptor antagonist, antiemetic, antipsychotic agent, anti-anxiety agent, antipruritic agent, serotonin receptor antagonist, or gastrointestinal agent. In some instances where the target dermatological condition is dermatitis, the neuromodulatory agent is not methanolic extract of Verbascum latisepalum Hub-Mor, and doxepin (3-(6H-benzo[c][1]benzoxepin-11-ylidene)-N,N-dimethylpropan-1-amine). In some instances where the target dermatological condition is dermatitis, the neuromodulatory agent is not phenylethanoid glycoside verbascoside, a methanolic extract from the leaves and flowers of the Verbascum species, an extract from the Verbascum species, dibenzoxepin tricyclic compound, a tricyclic antidepressant, antidepressant, adrenergic receptor antagonist, serotonin receptor antagonist, histamine receptor antagonist, non-selective monoamine reuptake inhibitor, or neuropsychiatric agent.

In some instances, the methods are method of treating psoriasis. Psoriasis is conventionally known as autoimmune skin disorder characterized by patches of scaling skin, redness, rashes, and blisters, Specific types of psoriasis that may be treated by methods of the invention include: plaque psoriasis, guttate psoriasis, inverse psoriasis, pustular psoriasis, erythrodermic psoriasis, and the like. In some instances where the target dermatological condition is psoriasis, the neuromodulatory agent is not a histamine receptor antagonist. In some instances where the target dermatological condition is psoriasis, the neuromodulatory agent is not cyclosporine ((3S,6S,9S,12R,15S,18S,21S,24S,30S,33S)-30-ethyl-33-[(E,1R,2R)-1-hydroxy-2-methylhex-4-enyl]-1, 4,7,10,12,15,19,25,28-nonamethyl-6,9,18,24-tetrakis(2-methylpropyl)-3,21-di(propan-2-yl)-1,4,7,10,13,16,19,22,25,28,31-undecazacyclotritnacontane-2,5,8,11,14,17,20,23,26,29,32-undecone), diphenoxylate (ethyl 1-(3-cyano-3,3-diphenylpropyl)-4-phenylpiperidine-4-carboxylate), or a cannabinoid receptor ligand. In some instances where the target dermatological condition is psoriasis, the agent is not a synthetic opioid, μ-opioid receptor antagonist, opioid agonist, calcineurin inhibitor, neuropsychiatric agent, antidiarrheal, anti-allergic agent, immunosuppressant, gastrointestinal agent, or cardiovascular agent. In some instances where the target dermatological condition is psoriasis, the neuromodulatory agent is not a neurokinin) (NK1) receptor antagonist or capsaicin ((E)-N-[(4-hydroxy-3-methoxyphenyl)methyl]-8-methylnon-6-enamide). In some instances where the target dermatological condition is psoriasis, the agent is not a capsaicinoid, antidepressant, anxiolytic, antiemetic, antipruritic, neuropeptide releasing agent, or analgesic. In some instances where the target dermatological condition is psoriasis, the neuromodulatory agent is not a selective serotonin re-uptake inhibitor (SSRI) or antidepressant. In some instances where the target dermatological condition is psoriasis, the neuromodulatory agent is not a nicotinic acetylcholine receptor (AChR) antagonist or anticholinergic agent.

In some instances, the methods are method of treating ulcers. Ulcers are conventionally known as sores on the external or internal lining of organs, caused by a break in a membrane, Specific types of ulcers that may be treated by methods of the invention include: diabetic ulcers, pressure ulcers, and stasis ulcers and the like. In some instances where the target dermatological condition is ulcers, the neuromodulatory agent is not olanzapine (2-methyl-4-(4-methylpiperazin-1-yl)-5H-thieno[3,2-c][1,5]benzodiazepine), neurotropin (an extract isolated from vaccinia virus-innoculated skin or tissues of rabbits), or an H2 receptor antagonist. In some instances where the target dermatological condition is ulcers, the neuromodulatory agent is not a benzodiazepine, D2 receptor antagonist, D3 receptor antagonist, D4 receptor antagonist, dopamine antagonist, alpha-1 adrenergic receptor antagonist, alpha adrenergic receptor antagonist, H1 receptor antagonist, H2 receptor antagonist, histamine receptor antagonist, muscarinic antagonist, serotonin uptake inhibitor, mood stabilizer, atypical antipsychotic, analgesic, neuropsychiatric agent, or cardiovascular agent. In some instances where the target dermatological condition is ulcers, the neuromodulatory agent is not sublingual fentanyl (N-phenyl-N-[1-(2-phenylethyl)piperidin-4-yl]propanamide), paracetamol/tramadol (N-(4-hydroxyphenyl)acetamide/(1R,2R)-2-[(dimethylamino)methyl]-1-(3-methoxyphenyl)cyclohexan-1 oxycodone ((4R,4aS,7aR,12bS)-4a-hydroxy-9-methoxy-3-methyl-2,4,5,6,7a,13-hexahydro-1H-4,12-methanobenzofuro[3,2-e]isoquinoline-7-one), morphine ((4R,4aR,7S,7aR,12bS)-3-methyl-2,4,4a,7,7a,13-hexahydro-1H-4,12-methanobenzofuro[3,2-e]isoquinoline-7,9-diol), buprenorphine ((2S)-2-[(5R,6R,7R,14S)-17-cyclopropylmethyl-4,5-epoxy-6,14-ethano-3-hydroxy-6-methoxymorphinan-7-yl]-3,3-dimethylbutan-2-ol), bupivacaine (1-butyl-N-(2,6-dimethylphenyl)piperidine-2-carboxamide). In some instances where the target dermatological condition is ulcers, the agent is not a fentanyl, anilide derivative, morphinan, alkaloid, oripavine, μ-opioid receptor agonist, opioid agonist, opioid receptor antagonist, endocannabinoid reuptake inhibitor, norepinephrine reuptake inhibitor, sodium channel blocker, serotonin reuptake inhibitor, 5-HT$_{2c}$ receptor antagonist, histamine receptor antagonist, serotonin receptor antagonist, serotonin releasing agent, semisynthetic opioid, euphoriant, narcotic analgesic, non-narcotic analgesic, anesthetic, non-steroidal anti-inflammatory drug, antipyretic, or neuropsychiatric agent. In some instances where the target dermatological condition is ulcers, the neuromodulatory agent is not erythropoietin, Yiqi Huayu, maropitant citrate ((2S,3S)-2-benzhydryl-N-[(5-tert-butyl-2-methoxyphenyl)methyl]-1-azabicyclo[2.2.2]octan-3-amine; 2-hydroxypropane-1,2,3-tricarboxylic acid; hydrate), or a TRPV1 antagonist. In some instances, the agent is not an erythrocyte cytokine, erythropoietic factor, glycoprotein hormone, herbal plant formula, NK$_1$ receptor antagonist, antiemetic, or analgesic. In some instances where the target dermatological condition is ulcers, the neuromodulatory agent is not sarpogrelate hydrochloride (4-[1-(dimethylamino)-3-[2-[2-(3-methoxyphenyl)ethyl]phenoxy]propan-2-yl]oxy-4-oxobutanoic acid; hydrochloride) or ketanserin (3-[2-[4-(4-fluorobenzoyl)piperidin-1-yl]ethyl]-1H-quinazoline-2,4-dione). In some instances where the target dermatological condition is ulcers, the agent is not a quinazoline, 5HT$_{2A}$ receptor antagonist, 5HT$_{2B}$ receptor antagonist, alpha-1 adrenergic receptor antagonist, histamine H1 receptor antagonist, platelet aggregation inhibitor, serotonin receptor antagonist, adrenergic receptor antagonist, histamine receptor antagonist, antihypertensive agent, anticoagulant, cardiovascular agent, or anti-allergic agent.

In some instances, the methods are method of treating acne. Acne is conventionally known as a skin disorder characterized by clogged hair follicles and inflammation of the skin, Specific types of acne that may be treated by methods of the invention include: non-inflammatory acne, inflammatory acne, whiteheads, blackheads, papules, pustules, nodules, cysts and the like. In some instances where the target dermatological condition is acne, the neuromodulatory agent is not desloratadine (8-chloro-11-piperidin-4-ylidene-5,6-dihydrobenzo[1,2]cyclohepta[2,4-b]pyridine), diphenhydramine (2-benzhydryloxy-N,N-dimethylethanamine), tea tree oil (essential oil steam-distilled from Melaleuca alternifolia), terfenadine (1-(4-tert-butylphenyl)-4-[4-[hydroxy(diphenyl)methyl]piperidin-1-yl]butan-1-ol), or a histamine H2 antagonist. In some instances where the target dermatological condition is acne, the agent is not an histamine H1 receptor antagonist, potassium channel blocker, muscarinic acetylcholine receptor antagonist, anticholinergic agent, sedative, antiemetic, anesthetic, histamine receptor antagonist, anti-allergic agent, antipruritic, essential oil, antiseptic. In some instances, where the target dermatological condition is acne, the neuromodulatory agent is not an ACh inhibitor, botulinum toxin, and neostigmine ([3-(dimethylcarbamoyloxy)phenyl]-trimethylazanium). In some instances where the target dermatological condition is acne, the agent is not a neurotoxin, skeletal muscle relaxant, neuromuscular blocking agent, acetylcholine release inhibitor, acetylcholinesterase inhibitor, cholinesterase inhibitor, parasympathomimetic agent, neuropsychiatric agent. In some instances, the agent does not decrease substance P.

In some instances, the methods are method of treating rosacea. Rosacea is conventionally known as a skin disorder characterized by redness of the face, fine red lines, acne, a swollen nose, and vision problems. Specific types of rosacea that may be treated by methods of the invention include: ocular rosacea, phymatous rosacea, papulopustular rosacea, erythematotelangiectatic rosacea and the like. In some instances where the target dermatological condition is rosacea, the neuromodulatory agent is not naloxone ((4R,4aS,7aR,12bS)-4a,9-dihydroxy-3-prop-2-enyl-2,4,5,6,7a,13-hexahydro-1H-4,12-methanobenzofuro[3,2-e]isoquinoline- 7-one), clonidine (N-(2,6-dichlorophenyl)-4,5-dihydro-1H-imidazol-2-amine), 1064-nm neodymium-yttrium aluminum garnet laser and pulsed dye laser, a TRPV1 and TRPA1 antagonist, pimecrolimus, tacrolimus, ondansetron (9-methyl-3-[(2-methylimidazol-1-yl)methyl]-2,3-dihydro-1H-carbazol-4-one), and botulinum toxin. In some instances where the target dermatological condition is rosacea, the agent is not a macrolide, κ-opioid receptor antagonist, δ-opioid receptor antagonist, μ-opioid receptor antagonist, opioid antagonist, morphinan, alpha-2 adrenergic receptor agonist, alpha-adrenergic receptor agonist, adrenergic receptor agonist, serotonin type 3 receptor antagonist, serotonin receptor antagonist, non-steroidal anti-inflammatory agent, disease modifying anti-rheumatic drug, antiemetic, analgesic, antipsychotic agent, anti-anxiety agent, antipruritic agent, skeletal muscle relaxant, neuromuscular blocking agent, acetylcholine release inhibitor, antihypertensive agent, immunosuppressant, or gastrointestinal agent.

In some instances, the methods are method of treating Rhytides (wrinkles). Rhytides (wrinkles) are conventionally known as folds or creases in the skin. Specific types of Rhytides (wrinkles) that may be treated by methods of the invention include: dynamic rhytides, static rhytides and the like. In some instances where the target dermatological condition is Rhytides (wrinkles), the neuromodulatory agent is not achillea millefolium extract or a medicinal plant extract. In some instances where the target dermatological condition is Rhytides (wrinkles), the neuromodulatory agent is not capsaicin ((E)-N-[(4-hydroxy-3-methoxyphenyl) methyl]-8-methylnon-6-enamide) or botulinum toxin type A and B. In some instances where the target dermatological condition is Rhytides (wrinkles), the agent is not capsaicinoid, antipruritic agent, analgesic, neurotoxin, skeletal muscle relaxant, neuromuscular blocking agent or acetylcholine release inhibitor. In some instances where the target dermatological condition is Rhytides (wrinkles), the neuromodulatory agent is not botulinum toxin type A and B or dimethylaminoethanol. In some instances where the target dermatological condition is Rhytides (wrinkles), the agent is not a neurotoxin, skeletal muscle relaxant, neuromuscular blocking agent, acetylcholine release inhibitor, antidepressant, nootropic, or anti-dyskinesia agent.

In some instances, the methods are method of treating Hyperhidrosis (excessive sweating). Hyperhidrosis (excessive sweating) is conventionally known as a condition characterized by sweating in excess of that required for normal thermoregulation. Specific types of Hyperhidrosis (excessive sweating) that may be treated by methods of the invention include: primary focal hyperhidrosis, secondary generalized hyperhidrosis and the like. In some instances where the target dermatological condition is Hyperhidrosis (excessive sweating), the neuromodulatory agent is not botulinum toxin type A and B and a nicotonic AChR antagonist. In some instances where the target dermatological condition is Hyperhidrosis, the agent is not a botulinum toxin, neurotoxin, skeletal muscle relaxant, neuromuscular blocking agent, acetylcholine release inhibitor, or anticholinergic agent.

In some instances, the methods are method of treating hyperpigmentation. Hyperpigmentation is conventionally known as a skin condition characterized by the overproduction of melanin in patches of skin. Specific types of hyperpigmentation that may be treated by methods of the invention include: postinflammatory hyperpigmentation, melasma/chloasma, ashy dermatosis, nevus of Ota and nevus of Ito, lentigo solarisand the like. In some instances where the target dermatological condition is hyperpigmentation, the neuromodulatory agent is not homochlorcyclizine (1-[(4-chlorophenyl)-phenylmethyl]-4-methyl-1,4-diazepan-4-ium; chloride), triamcinolone acetonide, fluocinolone acetonide, or a H2 receptor antagonist. In some instances where the target dermatological condition is hyperpigmentation, the agent is not a synthetic hydrocortisone derivative, histamine receptor antagonist, anticholinergic agent, group V corticosteroid, group VI corticosteroid, corticosteroid, anti-inflammatory agent, an anti-allergic agent, orimmunosuppressant.

Subjects that may be treated in accordance with the methods may be subjects that have been diagnosed as have a dermatological condition. As such, subjects that are treated in accordance with the invention may be subjects that have been diagnosed as having a diseases, disorders, symptoms, etc. involving the skin. A non-limiting list of dermatological conditions include, but are not limited to: dermatitis, e.g., atopic dermatitis, allergic contact dermatitis, irritant contact dermatitis, radiation dermatitis, seborrheic dermatitis; psoriasis; sunburn; ulcers, e.g., diabetic ulcers, pressure ulcers, and stasis ulcers; acne; rosacea; rhytides (wrinkles); hyperhidrosis (excessive sweating); hyperpigmentation; etc. Dermatological conditions can also arise from irritation and/or pain following laser or chemical resurfacing, dermabrasion therapy, cuts, burns, and abrasions.

In some instances, the methods include a step of diagnosing a subject for a dermatological condition. As such, in some instances the methods include diagnosing whether a subject has psoriasis. In some instances, the methods include diagnosing whether a subject has dermatitis. In some instances, the method includes diagnosing whether a subject has rosacea. In some instances, the methods include diagnosing whether a subject has acne. In some instances, the methods include diagnosing whether a subject has Rhytides. In some instances, the methods include diagnosing whether a subject has an ulcer. In some instances, the methods include diagnosing whether a subject has hyperpigmentation. In some instances, the methods include diagnosing whether a subject has hyperhidrosis. Any convenient method of diagnosing a subject for a given determatological condition may be employed, including methods known to those of skill in the art.

Aspects of the methods of certain embodiments include obtaining biometric data from a subject and employing the biometric data to diagnose the subject for the present of a target dermatological condition. The phrase "biometric data" is employed to refer to a measure of a biometric parameter that relates to the physiology of a living organism, e.g., as described below. As such, the biometric parameter which is employed in methods of the invention to obtain the biometric data may be a parameter that provides information about an organism's vital functions, including growth and development, the absorption and processing of nutrients, the synthesis and distribution of proteins and other organic molecules, the functioning of different tissues, organs, and other anatomic structures; the psychological and/or behavioral state of the subject, e.g., mental and/or cognitive state of the subject, which may be subjective or objective, self-reported or third party observed, as desired; etc. The obtained biometric data may be static biometric data, or dynamic biometric data, e.g., as described above. In some instances, the biometric data is a data that is obtain from a nervous system component or that can be used as a proxy for a nervous system component, such as that it may be viewed as nervous system biometric data.

Biometric parameters that are measured may vary widely, where examples of such parameters include physiological, chemical, electrical, behavioral, psychological, etc., based parameters, as well as variations and derivatives thereof. Biometric parameters of interest include, but are not limited to: physical parameters, e.g., blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastrointestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; nerve conduction measures, e.g., motor NCS, sensory NCS, F-wave study, H-reflex study, spf-NCS, etc.; and the like, and combinations thereof; sample analysis obtainable parameters, e.g., pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apolipoprotein B100/A1 ratio, white blood cell count, cholesterol, oxygen saturation, and the like, and combinations thereof. Dynamic biometric data may be made up of information about a single type of biometric parameter, or two or more different types of biometric parameters. The biometric data employed in methods of the invention may thus be made up of information obtained by measuring or assessing one or more biometric parameters, such as the ones listed above.

As summarized above, the biometric data that is obtained and employed in embodiments of the invention may be either static biometric data or dynamic biometric data. By "dynamic biometric data" is meant biometric data that incorporates some type of change component, as opposed to static biometric data. The change component may vary widely, where examples of change components include, but are not limited to components that are: temporal and/or in response to an applied stimulus and/or in response to withdrawal of stimulus and/or in response to a change in the contextual environment of the subject. For example, the dynamic biometric data that is obtained may be biometric data obtained over a given period of time. The given period of time may vary, ranging in some instances from 0.1 seconds to 24 hours, such as 1 second to 12 hours, e.g., 1 second to 1 hour, including 1 second to 1 minute. Where the dynamic biometric data is data obtained over a given period of time, the data may be obtained continuously over that period of time or at one or more distinct points during that period of time. For example, the biometric parameter(s) that is monitored in order to obtain biometric data may be monitored continuously during the given period of time, i.e., it may be obtained in an uninterrupted manner, i.e., without cessation, during the given period of time. Alternatively, the biometric parameter(s) that is monitored in order to obtain biometric data may be monitored intermittently during the given period of time, i.e., it may be obtained at one or more points over the given period of time, with an interval between points at which it is not obtained. In some embodiments, the interval may vary, ranging, for example, from 0.01 sec to 60 minutes or longer, such as 0.1 to 60 s. In some instances, the dynamic biometric data is obtained by evaluating a biometric parameter for a rate of change over a period of time. As such, methods may include obtaining information about the speed at which a biometric parameter of interest changes over a given period of period of time. Obtaining dynamic biometric data as described above provides for numerous benefits, including increases in temporal resolution, as compared to single point in time data. Dynamic biometric data as obtained herein provides a truer and more meaningful measure of the biometric value(s) of interest, as compared to single point in time measurements.

Dynamic biometric data of interest also include biometric data that is obtained by evaluating a biometric parameter for a change in response to an applied stimulus. Such biometric data may include data that is obtained before and/or after application of the stimulus to the subject. In some instances, the biometric data may be obtained over a given period of time that spans or follows the application of the stimulus to the subject. This type of biometric data may be viewed as biometric data that is obtained over a given period of time in conjunction with application of a stimulus to the subject being evaluated. The applied stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also include biometric data that is obtained by evaluating a biometric parameter for a change in response to withdrawal of a stimulus. Such biometric data may include data that is obtained before and/or after withdrawal (e.g., blockage) of the stimulus to the subject. In some instances, the biometric data may be obtained over a given period of time that spans or follows the withdrawal of the stimulus to the subject. This type of biometric data may be viewed as biometric data that is obtained over a given period of time in conjunction with withdrawal of a stimulus to the subject being evaluated. The withdrawn stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also include biometric data that is obtained by evaluating a biometric parameter for a change in response to modulation of the contextual environment of the subject. By contextual environment of the subject is meant the perceived environment of the subject. Such biometric data may include data that is obtained before and/or after the modulation in the contextual environment of the subject. In some instances, the biometric data may be obtained over a given period of time that spans or follows the modulation of the contextual environment of the subject. This type of biometric data may be viewed as biometric data that is obtained over a given period of time in conjunction with modulation of the contextual environment of the subject. The modulation of the contextual environment of the subject may vary, where contextual modulations of interest include, but are not limited to, change in day and night duration, change in temperature, change in humidity, change in elevation, change in atmosphere, and the like.

Dynamic biometric data of interest also include biometric data that is obtained by evaluating a biometric parameter for a change in response to modulation of the behavioral aspect of the subject. By behavioral aspect of the subject is meant an observable activity of the subject. Such biometric data may include data that is obtained before and/or after the modulation of the behavioral aspect of the subject. In some instances, the biometric data may be obtained over a given period of time that spans or follows the modulation of the behavioral aspect of the subject. This type of biometric data may be viewed as biometric data that is obtained over a given period of time in conjunction with modulation of the behavioral aspect of the subject. The modulation of the behavioral aspect of the subject may vary, where behavioral modulations of interest include, but are not limited to, dietary changes, sleep pattern changes, activity level changes, and the like.

As reviewed above, a variety of different biometric parameters may be measured to obtain the biometric data of interest. The method by which the biometric data is obtained may vary depending on the nature of the biometric parameter that is monitored. In some instances, the method employed to obtain the biometric data includes physically monitoring the subject to obtain the biometric data. For example, physical monitoring of the subject may be employed where the biometric parameter is one or more of blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastrointestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; brain activity, function and structure related biometric data, e.g., as captured by functional Magnetic Resonance Imaging (fMRI), magnetoencephalography (MEG) and electroencephalography (EEG); nerve conduction measures, e.g., motor NCS, sensory NCS, F-wave study, H-reflex study, spf-NCS, etc.; and combinations thereof. Any convenient protocol for physically monitoring a subject for one or more of the above biometric parameters may be employed, and methods for physically monitoring each are known in the art. For example, where the biometric parameter of interest is HRV, the physical monitoring may include measures such as low frequency peak ("LF"), high frequency peak ("HF"), and the LF/HF ratio to determine HRV and obtain the HRV derived biometric data. Other methods of obtaining biometric data of interest include, but are not limited to: retinal scan, photograph and video images; and the like.

In some embodiments, the biometric data is obtained by a method that includes analyzing a sample from the subject to obtain the biometric data. The sample that is analyzed may vary, where samples of interest include, but are not limited to: urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, and the like, and may employ conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like. Biometric parameters that may be monitored by evaluating a sample from the subject include, but are not limited to: pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apoloipoprotein B100/A1 ratio, white blood cell count, cholesterol, oxygen saturation, and combinations thereof.

Any convenient protocol for physically monitoring a subject for one or more of the above biometric parameters may be employed, and methods for testing a sample for monitoring each are known in the art. In some instances, the dynamic biometric data is obtained by both physically monitoring the subject and by assaying a sample from the subject, e.g., as described above.

Aspects of the methods further include diagnosing the subject as having a dermatological condition based, at least in part, on the obtained biometric data. As such, following obtainment of the biometric data, the subject is evaluated for a target dermatological condition based on the obtained biometric data. Any convenient protocol may be employed to evaluate the subject for the target dermatological condition based on the obtained biometric data. For example, the obtained biometric data may be compared to control or reference sets of biometric data to obtain the dermatological condition evaluation. In some instances, the obtained biometric data may be compared to a suitable database of control or reference sets to obtain the dermatological condition evaluation. The control or references sets of data may be made up of data obtained from multiple different individuals of known dermatological conditions. The data may be made up from individuals of a variety of different ages and health, including from young and old individuals, as well as healthy and diseased individuals, as desired. Any suitable comparison algorithm may be employed, and the output dermatological condition evaluation may be produced in a variety of different formats or configurations. This dermatological evaluation step may be performed using a suitable functional module of a computing device/system, e.g., as desired.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Also provided are kits for practicing the subject methods. The subject kits may include a neuromodulatory agent, such as pharmacological or electrical agent, e.g., as described above. The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. Some or all components of the subject kits may be packaged in suitable packaging to maintain sterility. In some embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

The following examples are offered by way of illustration, and not by way of limitation.

EXPERIMENTAL

Example 1. Dermatological Condition Diagnosis

A patient presents with a dermatologic abnormality. A diagnostic device which samples neurophysiologic information in the patient, not necessarily directly related to the skin findings, is employed. The device samples the data in time-series, and continuously. A measured, standardized dose of stress is applied to the patient. An example is a 50 meter walk in 30 seconds. The time duration of homeostatic response (recovery of the neurophysiologic data back to baseline) is measured to assess the degree of autoregulatory capacity of the body's neurophysiologic system. Examples of sampled neurophysiologic metrics include heart rate, blood pressure, pH, oxygenation. The correlation of these metrics, and the time duration to normalize these metrics after the standardized exposure to stress, is mapped to dermatologic illnesses and severity.

Example 2. Treatment of a Dermatological Condition

A patient presents with a dermatologic abnormality. A medical device, pharmacological agents, behavioral or psychological modification which modulates the autoregulatory capacity of the neurophysiologic systems in the body in a way that improves the dermatologic symptoms is employed. Specifically, the therapy improves the ability of the neurophysiologic systems to respond to stress, as a way to improve dermatologic symptoms.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject for a dermatological condition, the method comprising:
obtaining biometric data from a neurophysiologic system of the subject to assess the autoregulatory capacity of the neurophysiologic system, wherein obtaining biometric data from the neurophysiologic system of the subject comprises applying a stress to the subject; and
administering an effective amount of a neuromodulatory agent to the subject to treat the subject for the dermatological condition, wherein the neuromodulatory agent is a cholinergic system modulator and the dermatological condition is psoriasis.

2. The method according to claim 1, wherein the subject is a mammal.

3. The method according to claim 2, wherein the subject is a human.

4. The method according to claim 1, wherein the cholinergic system modulator is chosen from acetylcholine, atropine, ambenonium, arecholine, atropine methyl-nitrate, benztropine, bethanechol, biperiden, botulinum toxin, carbachol, cevimeline, curare (d-Tubocurarine), cyclopentolate, demecarium, echothiophate, edrophonium, glycopyrrolate, hemicholinium, hexamethonium, homatropine, ipratropium, isoflurophate (DFP), malathion, mecamylamine, methacholine, methscopolamine, muscarine, neostigmine, nicotine, parathion, physostigmine, pilocarpine, pirenzepine, propantheline, pyridostigmine, sarin, scopolamine, soman, succinylcholine, tabun, trihexyphenidyl, trimethaphan, tropicamide, varenicline, galantamine hydrobromide, suxamethonium chloride, epibatidine, atracurium, doxacurium, mivacurium, pancuronium, tubocurarine, vecuronium, 18-methoxycoronaridine, dextromethorphan, dextrorphan, 3-methoxymorphinan, oxotremorine, dicyclomine, doxylamine, orphenadrine, oxitropium, oxybutynin, tolterodine, tiotropium, solifenacin, bupropion, hyoscyamine, ambenomium, donepezil, rivastigmine, tacrine, pralidoxime, cisatracurium, metocurine, rocuronium, oxybutynine, trospium, dihexyverine, prifinium, propantheline, tiemonium, benzhexol, tropatepine, biperidene, and botulinum toxin.

5. The method according to claim 1, wherein administering an effective amount of the neuromodulatory agent to the subject to treat the subject for the dermatological condition comprises modulating the autoregulatory capacity of the neurophysiologic system.

6. The method according to claim 1, wherein the biometric data is selected from heart rate, blood pressure, pH, and oxygenation.

* * * * *

UNITED STATES PATENT AND TRADEMARK OFFICE
CERTIFICATE OF CORRECTION

| | |
|---|---|
| PATENT NO. | : 11,383,084 B2 |
| APPLICATION NO. | : 15/965209 |
| DATED | : July 12, 2022 |
| INVENTOR(S) | : Anthony Joonkyoo Yun et al. |

It is certified that error appears in the above-identified patent and that said Letters Patent is hereby corrected as shown below:

In the Specification

Please replace "cyclohexan-1" with -- cyclohexan-1-ol -- (Column 43, Line 51).

Signed and Sealed this
Twenty-third Day of August, 2022

Katherine Kelly Vidal
*Director of the United States Patent and Trademark Office*